(12) United States Patent
Kabanov et al.

(10) Patent No.: US 9,974,866 B2
(45) Date of Patent: May 22, 2018

(54) PROTEIN-POLY(2-OXAZOLINE) CONJUGATES FOR ENHANCED CELLULAR DELIVERY AND TRANSPORT ACROSS BIOLOGICAL BARRIERS

(75) Inventors: Alexander V. Kabanov, Omaha, NE (US); Jing Tong, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days. days.

(21) Appl. No.: 13/634,717

(22) PCT Filed: Apr. 7, 2011

(86) PCT No.: PCT/US2011/031542
§ 371 (c)(1),
(2), (4) Date: Oct. 4, 2012

(87) PCT Pub. No.: WO2011/127256
PCT Pub. Date: Oct. 13, 2011

(65) Prior Publication Data
US 2013/0017166 A1    Jan. 17, 2013

Related U.S. Application Data

(60) Provisional application No. 61/321,617, filed on Apr. 7, 2010.

(51) Int. Cl.
*A61K 31/00* (2006.01)
*A61K 47/59* (2017.01)
*A61K 38/00* (2006.01)

(52) U.S. Cl.
CPC .............. *A61K 47/59* (2017.08); *A61K 38/00* (2013.01)

(58) Field of Classification Search
CPC .... A61K 31/74; A61K 31/785; A61K 31/787; A61K 47/48; A61K 47/48169; A61K 47/48176; A61K 47/48215; B82Y 5/00; C08F 255/02; C08F 279/02; B08F 297/04; C08G 63/181; C08G 63/183
See application file for complete search history.

(56) References Cited

U.S. PATENT DOCUMENTS

| | | | |
|---|---|---|---|
| 7,056,532 B1 | 6/2006 | Kabanov | |
| 7,169,411 B1 | 1/2007 | Kabanov et al. | |
| 8,107,151 B1 | 1/2012 | Ptasinski et al. | |
| 8,168,222 B2 | 5/2012 | Kabanov et al. | |
| 2004/0110735 A1* | 6/2004 | Ekwuribe | A61K 47/48215 514/182 |
| 2006/0051317 A1* | 3/2006 | Batrakova et al. | 424/78.37 |
| 2008/0145416 A1 | 6/2008 | Bronich et al. | |
| 2010/0041592 A1 | 2/2010 | Kabanov et al. | |
| 2010/0291065 A1 | 11/2010 | Kabanov et al. | |

OTHER PUBLICATIONS

Luxenhofer et al. First poly(2-oxazoline)-peptide conjugate for targeted radionuclide cancer therapy. Abstr. Pap. Am. Chem. Soc., vol. 232, American Chemical Society National Meeting, San Francisco, CA, USA, Sep. 10-14, 2006.*
Luxenhofer et al. First poly(2-oxazoline)-peptide conjugate for targeted radionuclide cancer therapy. Proc. Abstr. Pap. Am. Chem. Soc. vol. 232, ACS National Meeting, San Francisco, CA, USA, 2006.*
Aoi et al. Synthesis and assembly of novel chitin derivatives having amphiphilic polyoxazoline block copolymer as a side chain. Macromol. Chem. Phys. 1999; 200: 1112-1120.*
Luxenhofer et al. Biomaterials. 2010; 31: 4972-4979. (Available online Mar. 26, 2010).*
Luxenhofer, R., et al. "Doubly amphiphilic poly(2-oxazoline)s as high-capacity delivery systems for hydrophobic drugs." Biomaterials. Jun. 2010;31(18):4972-9. Epub Mar. 26, 2010.
Mero, A., et al. "Synthesis and characterization of poly(2-ethyl 2-oxazoline)-conjugates with proteins and drugs: suitable alternatives to PEG-conjugates?" J Control Release. Jan. 22, 2008;125(2):87-95. Epub Oct. 22, 2007.
Hoogenboom, R. "Poly(2-oxazoline)s: a polymer class with numerous potential applications." Angew Chem Int Ed Engl. 2009;48(43):7978-94.
Cesana, S., et al. "First Poly(2-oxazoline)s with Pendant Amino Groups." Macromol. Chem. Phys. 2006;207:183-192.
Naka, K., et al. "Aggregates of peptide-containing block copolymers and their interactions with a lipase in aqueous solution." Macromol. Chem. Phys. 1997;198:89-100.
Tong, J., et al. "Protein Modification with Amphiphilic Block Copoly(2-oxazoline)s as a New Platform for Enhanced Cellular Delivery." Mol. Pharm. Aug. 2, 2010;7(4):984-992.
Tong, J., et al. "Protein-Poly(2-oxazoline) Conjugation: Synthesis, Characterization and Enhanced Cellular Uptake." In Nanomedicine and Drug Delivery Symposium Abstract Book. Indianapolis, IN. Oct. 5, 2009. p. 90.
Tong, J., et al., "Conjugates of Superoxide Dismutase 1 with Amphiphilic Poly(2-oxazoline) Block Copolymers for Enhanced Brain Delivery: Synthesis, Characterization and Evaluation in Vitro and in Vivo," Mol. Pharm. (2013) 10:360-377.
Gaertner, F.C., et al., "Synthesis, biodistribution and excretion of radiolabeled poly(2-alkyl-2-oxazoline)s" J. Control. Rel. (2007) 119:291-300.
Cambon, A., et al., "Cytocompatibility and P-glycoprotein Inhibition of Block Copolymers: Structure-Activity Relationship" Mol. Pharm. (2013) 10:3232-3241.

* cited by examiner

*Primary Examiner* — David Browe
(74) *Attorney, Agent, or Firm* — Robert C. Netter, Jr.; Dann, Dorfman, Herrell and Skillman

(57) ABSTRACT

The present invention provides polymer-polypeptide conjugates comprising a poly(2-oxazoline) amphiphilic block copolymer linked to a polypeptide and methods of use thereof.

20 Claims, 13 Drawing Sheets

US 9,974,866 B2

Figure 1:
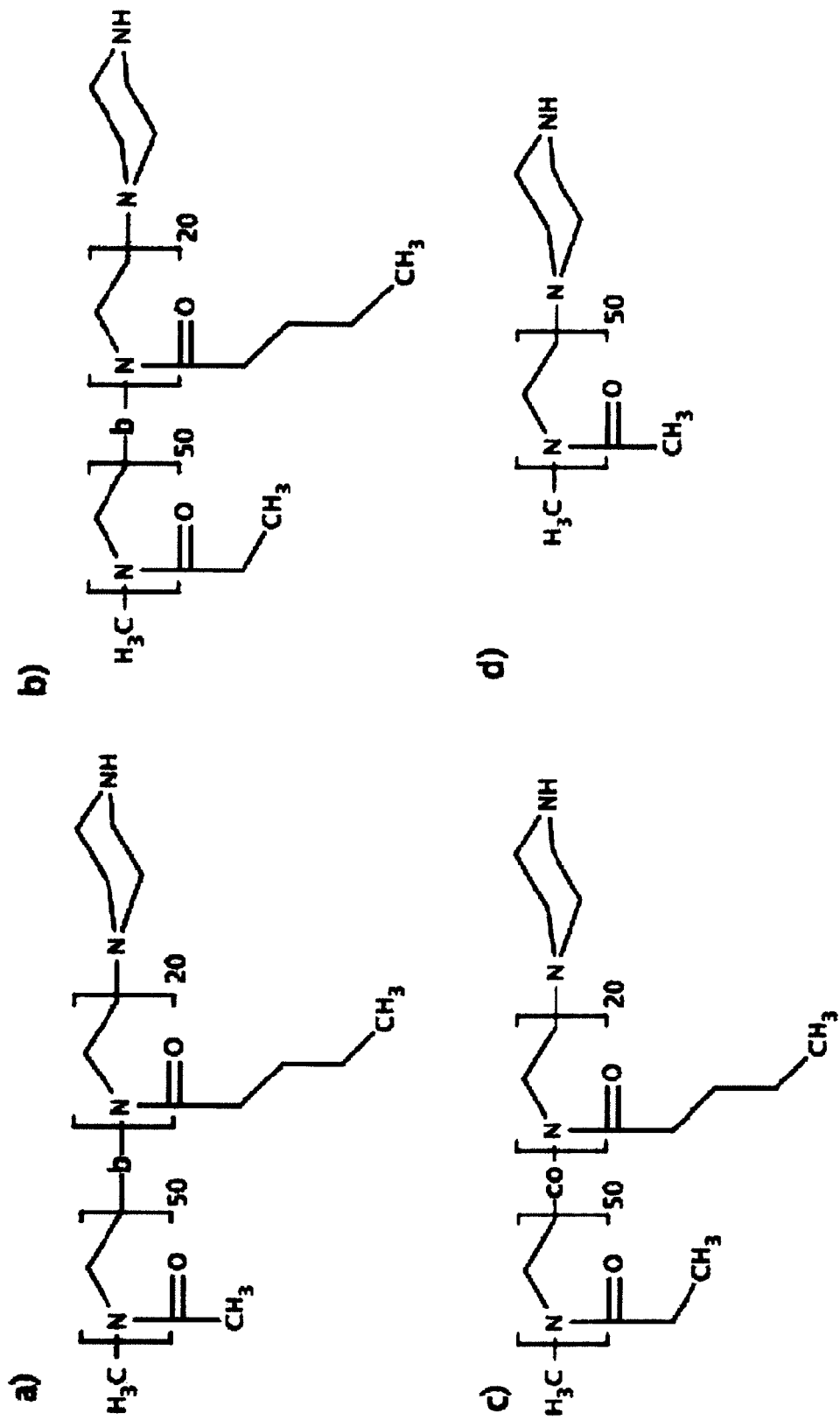

PROTEIN-POLY(2-OXAZOLINE) CONJUGATES FOR ENHANCED CELLULAR DELIVERY AND TRANSPORT ACROSS BIOLOGICAL BARRIERS

This application is a § 371 application of PCT/US2011/031542, filed Apr. 7, 2011, which claims priority under 35 U.S.C. § 119(e) to U.S. Provisional Patent Application No. 61/321,617, filed on Apr. 7, 2010. The foregoing applications are incorporated by reference herein.

This invention was made with government support under Grant No. NS051334 awarded by the National Institutes of Health. The government has certain rights in the invention.

FIELD OF THE INVENTION

The present invention relates generally to amphiphilic polymer conjugates and methods of use thereof. The present invention also relates to compositions and methods for the delivery of therapeutic, diagnostic, and cosmetic agents to a patient.

BACKGROUND OF THE INVENTION

Development of therapeutic proteins is one of the most thriving areas in today's pharmaceutical and biotech industry. However, many limitations of protein drugs need to be overcome before they can be successfully landed in the marketplace (Brown, L. R. (2005) Expert Opin. Drug Deliv., 2:29-42; Malik et al. (2007) Curr. Drug Deliv., 4:141-151). One of the major problems of protein drugs is their inability to cross physiological barriers, such as intestinal epithelial cell layer and the blood-brain barrier (Singh et al. (2007) J. Pharm. Sci., 97:2497-2523; Begley, D. J. (2004) Pharmacology & Therapeutics 104:29-45). Amphiphilic triblock copolymers comprising poly(ethylene oxide)-b-poly(propylene oxide)-b-poly(ethylene oxide) (PEO-PPO-PEO), also known as Pluronic®, were conjugated with a model protein, horseradish peroxidase (HRP) (Yi et al. (2008) Bioconjug. Chem., 19:1071-1077; Batrakova et al. (2005) Bioconjug. Chem., 16:793-802). It was found that HRP-Pluronic® conjugates can efficiently internalize into cells and cross the blood-brain barrier model both in vitro and in vivo (Yi et al. (2008) Bioconjug. Chem., 19:1071-1077; Batrakova et al. (2005) Bioconjug. Chem., 16:793-802). Furthermore, HRP modified by lipophilic fatty acid also exhibited enhanced cellular uptake and higher permeability across the blood-brain barrier (Batrakova et al. (2005) Bioconjug. Chem., 16:793-802; Slepnev et al. (1995) Bioconjug. Chem., 6:608-615). These results may suggest that after modification, the hydrophobic segment of protein conjugates can facilitate binding between water-soluble proteins and cell membranes, and enhance cellular uptake and transcellular transport of such proteins (Batrakova et al. (2005) Bioconjug. Chem., 16:793-802). New polymers for transporting conjugated proteins into cells and across biological barriers are desired.

SUMMARY OF THE INVENTION

In accordance with the instant invention, compositions and methods are provided for the delivery of compounds to a cell and/or across a histohematic barrier. In a particular embodiment, conjugates comprising at least one amphiphilic copolymer linked (e.g., covalently linked) to at least one compound of interest are provided. In a particular embodiment, the compound of interest is a polypeptide (e.g., a protein or peptide). In another embodiment, the amphiphilic copolymer is an amphiphilic block copolymer, particularly one comprising at least one hydrophilic segment comprising at least one hydrophilic poly(2-oxazoline), and at least one hydrophobic segment comprising at least one hydrophobic poly(2-oxazoline). In a particular embodiment, the hydrophilic segment is poly(2-methyl-2-oxazoline) or poly(2-ethyl-2-oxazoline) and the hydrophobic segment is poly(2-alkyl-2-oxazoline) (e.g., poly(2-butyl-2-oxazoline)). Compositions comprising at least one conjugate and at least one carrier (e.g., a pharmaceutically acceptable carrier) are also provided.

In accordance with another aspect of the instant invention, methods for delivering at least one compound (e.g., polypeptide) to a subject or cell are provided. The methods comprise administering or contacting at least one composition of the instant invention to a subject, cell, or tissue.

In accordance with yet another aspect of the instant invention, methods of treating a disorder or disease in a patient in need thereof are provided. The methods comprise administering at least one composition of the instant invention to the patient.

BRIEF DESCRIPTIONS OF THE DRAWING

FIG. 1 provides structures of the following poly(2-oxazoline)s: P(MeOx$_{50}$-b-BuOx$_{20}$) (FIG. 1A); P(EtOx$_{50}$-b-BuOx$_{20}$) (FIG. 1B); P(EtOx$_{50}$-co-BuOx$_{20}$) (FIG. 1C); and PMeOx$_{50}$ (FIG. 1D).

Figure 2:
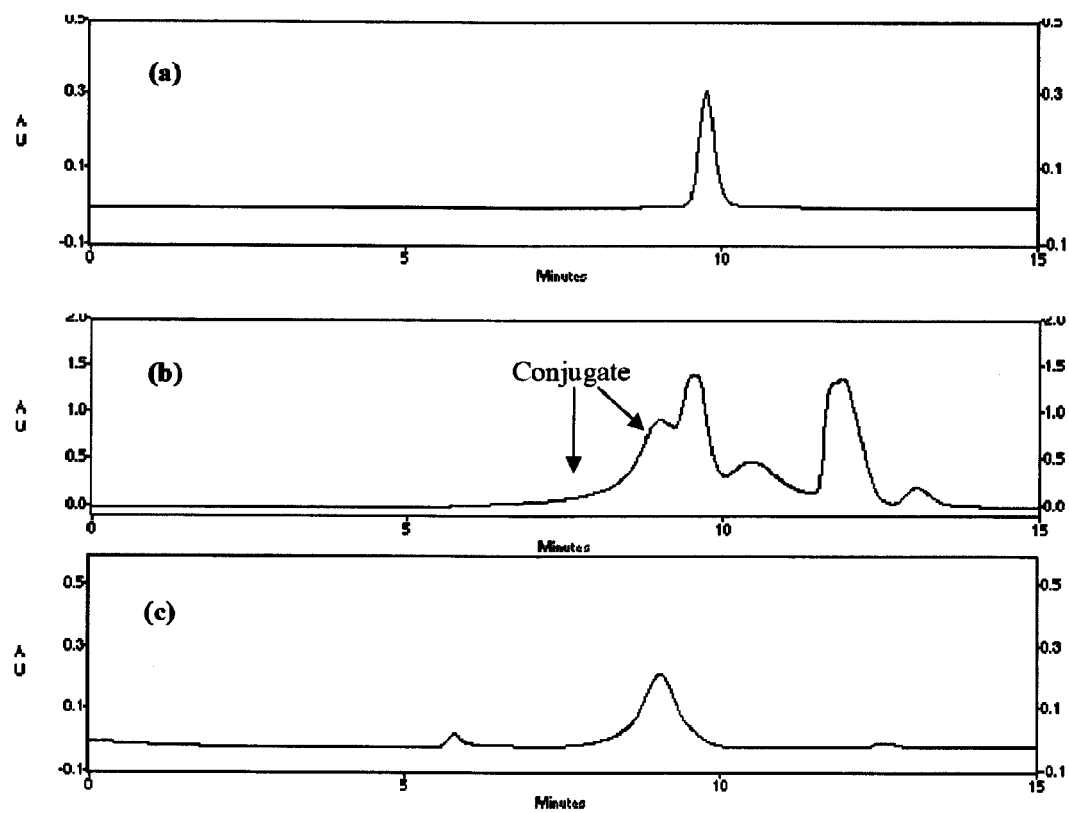

FIG. 2 provides representative chromatographic profiles of HRP-poly(2-oxazoline) conjugates purification using TSKgel® G3000SWXL column (0.78 cm×30 cm): HRP (FIG. 2A); reaction mixture of HRP×P(MeOx-b-BuOx) (FIG. 2B); and HRP×P(MeOx-b-BuOx) (FIG. 2C), after purification. UV absorbance was detected at 220 nm. The mobile phase was methanol (5%) and pH 6.8, 0.1 M NaH$_2$PO$_4$, 0.2M NaCl buffer (95%).

Figure 3:
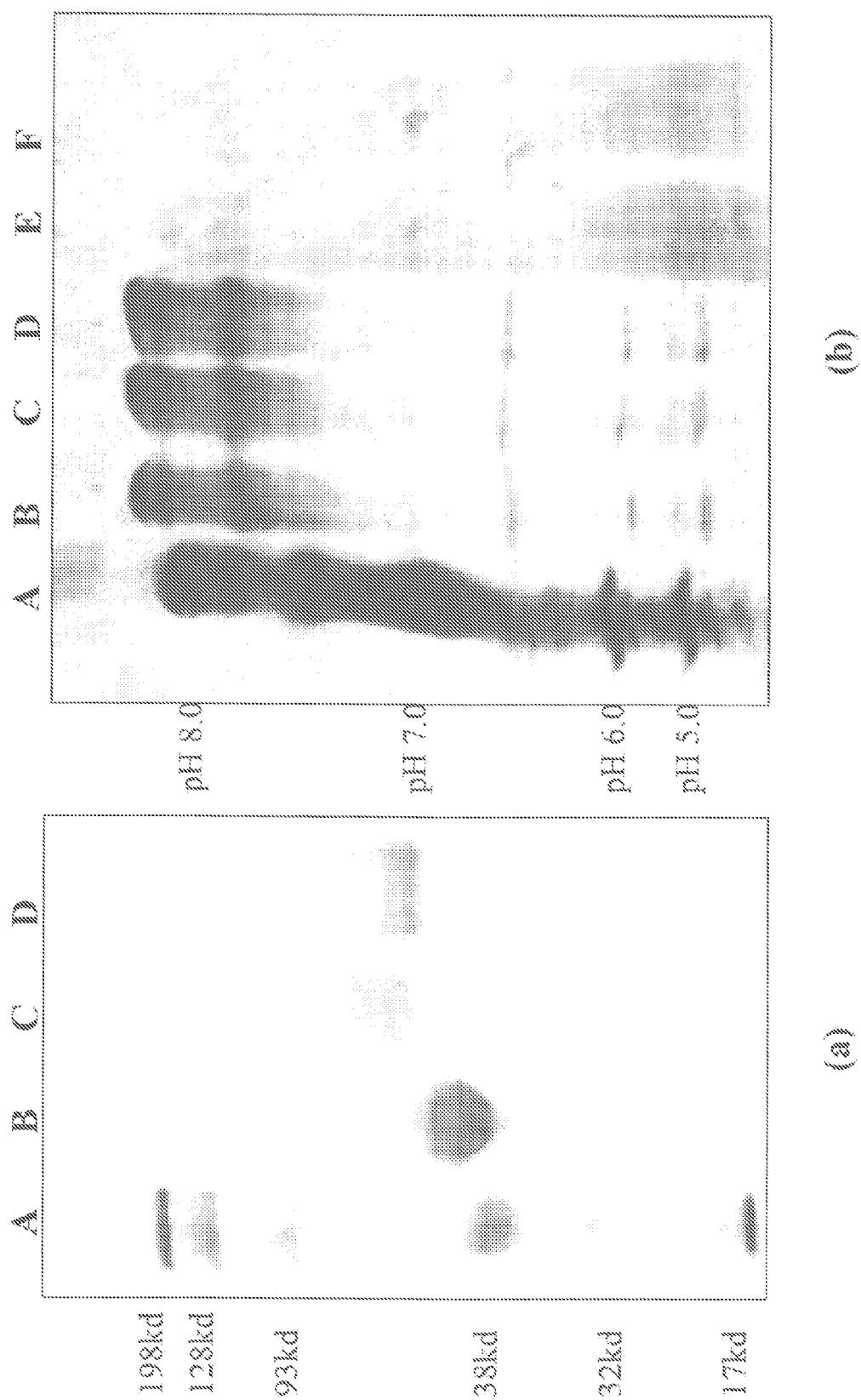

FIG. 3 provides representative SDS-PAGE (FIG. 3A) and IEF analysis (FIG. 3B) of HRP and HRP×POx: In FIG. 3A: A—Ladder; B—HRP; C—HRP×P(MeOx-b-BuOx); and D-HRP×P(EtOx-b-BuOx). In FIG. 3B: A—Ladder; B—HRP; C—mixture of HRP and P(MeOx-b-BuOx) (1:10); D—mixture of HRP and P(EtOx-b-BuOx) (1:10); E—HRP×P(MeOx-b-BuOx); and F—HRP×P(EtOx-b-BuOx).

Figure 4:
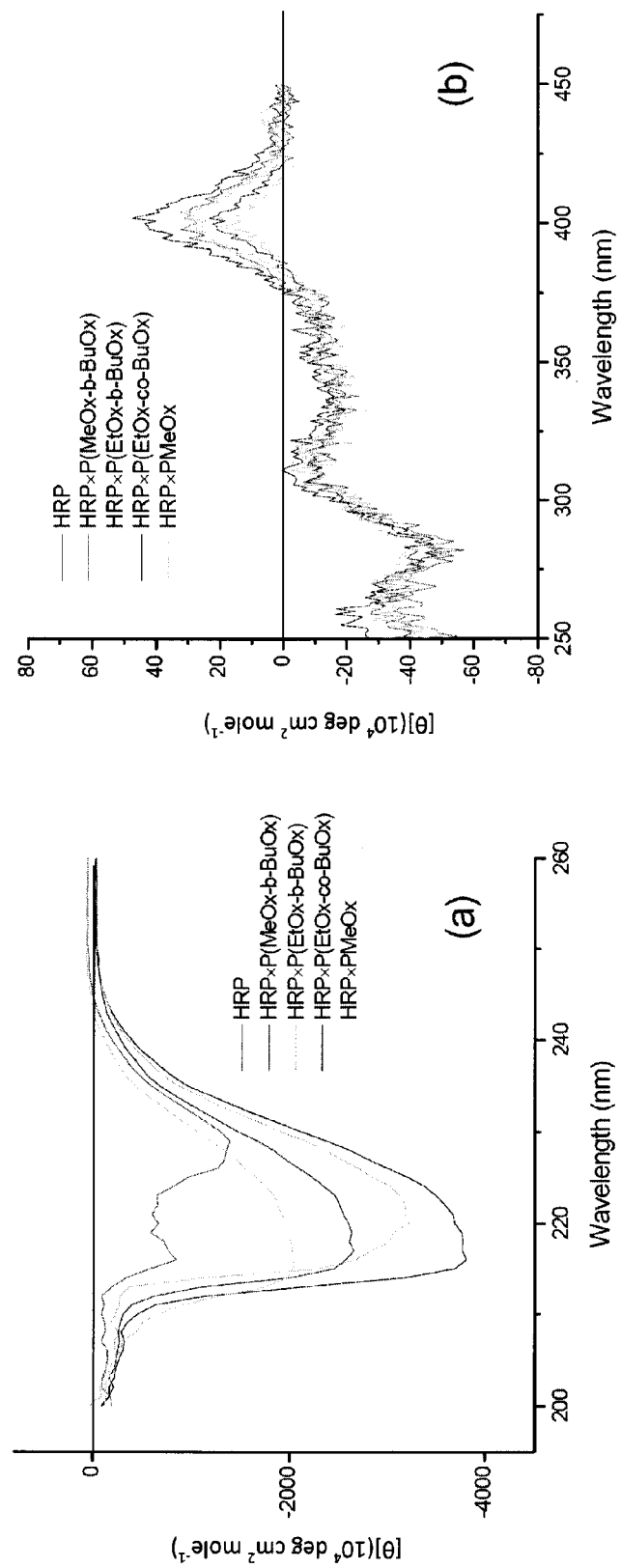

FIG. 4 provides CD spectra of HRP and HRP-poly(2-oxazoline)s, FIG. 4A: Far-UV (200-260 nm) CD, and FIG. 4B: Near-UV-vis (250-450 nm) CD. All samples were dissolved in PBS (pH 7.4) at the concentration of 0.5 mg/ml (determined by MicroBCA). The modification degrees of HRP-poly(2-oxazoline)s are the same as those in cellular uptake studies.

Figure 5:
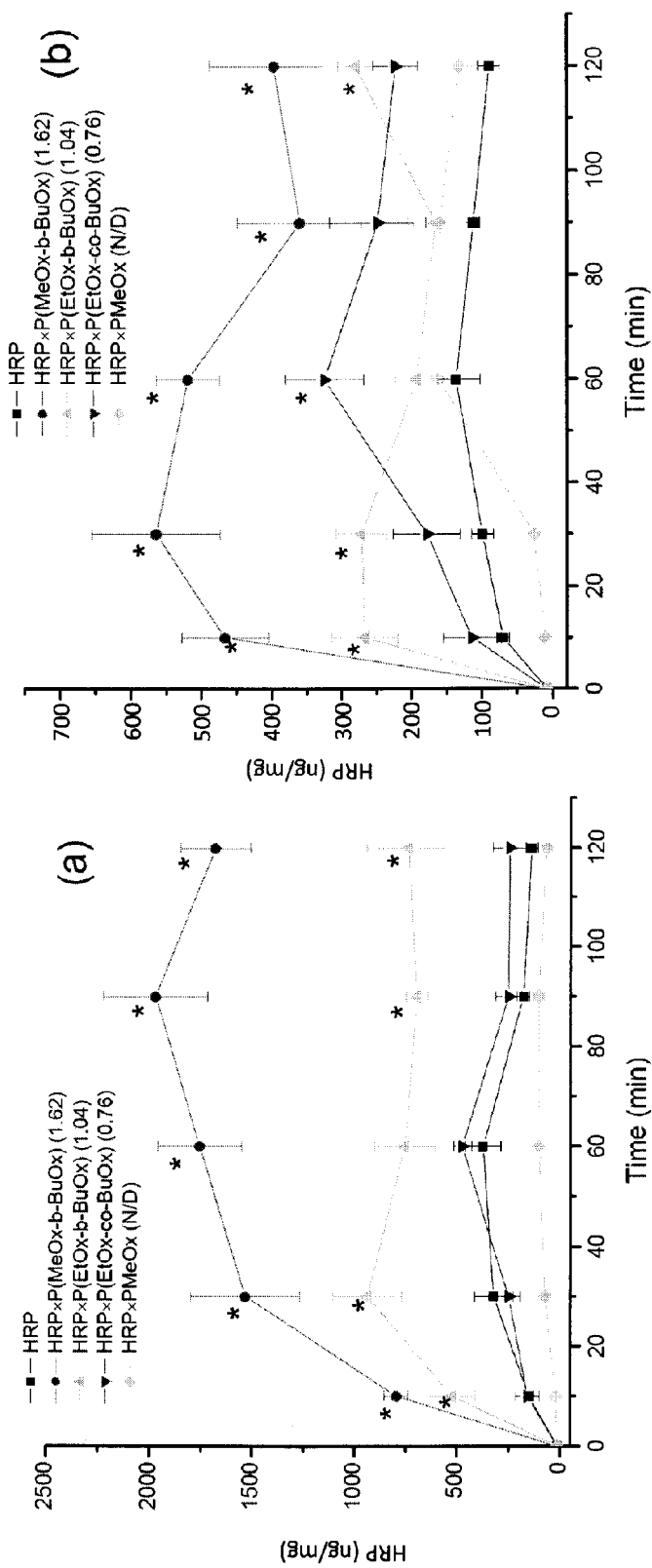

FIG. 5 provides graphs showing cellular uptake of HRP and HRP-poly (2-oxazoline)s in MDCK cells (FIG. 5A) and Caco-2 cells (FIG. 5B). The modification degrees of the conjugates are shown in the brackets. Data presented as means±SEM (n=6). Statistical analysis was done using one-way ANOVA (LSD multiple comparisons). The symbol * indicates statistical significance (p<0.05).

Figure 6A:
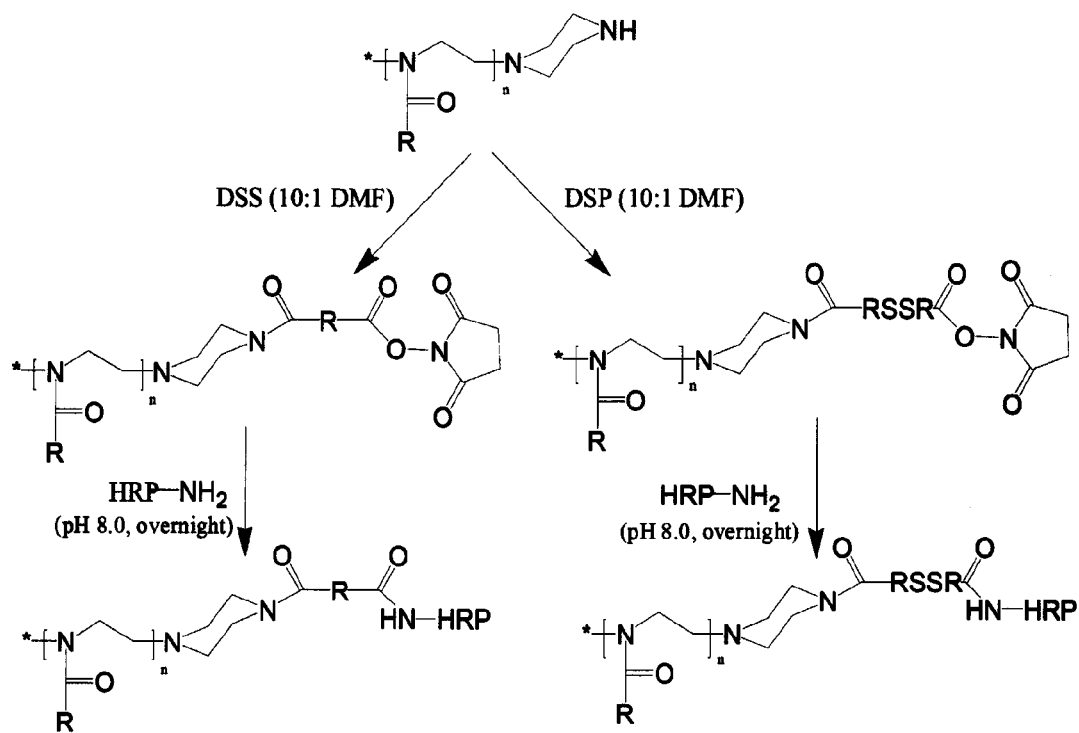
Figure 6B:
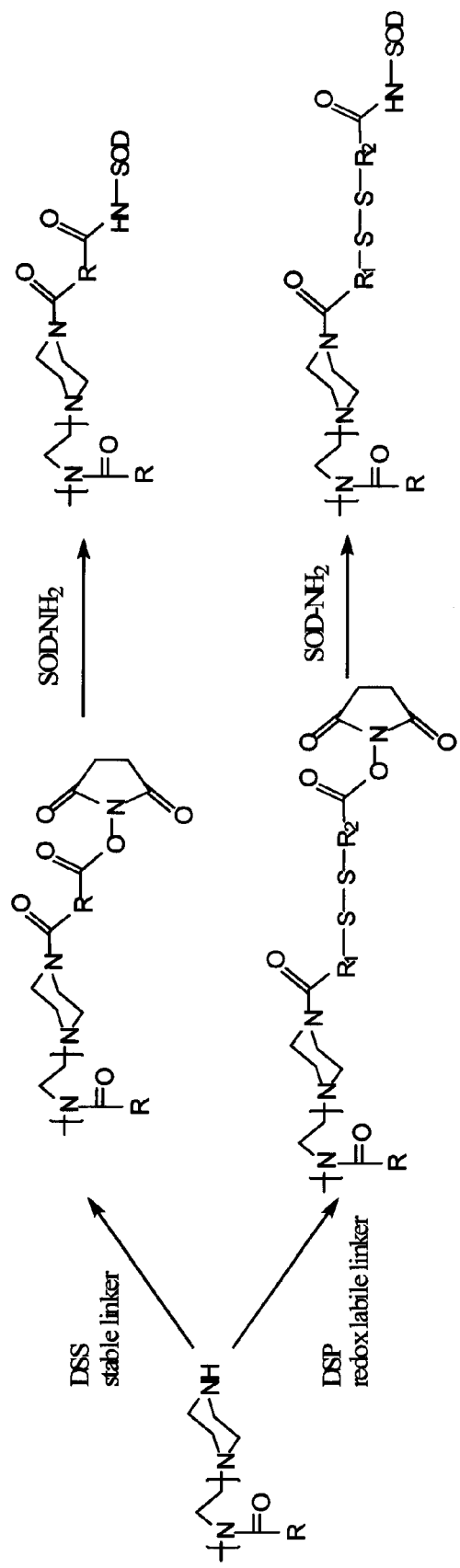

FIG. 6A provides synthetic routes for HRPxPOx using DSS and DSP linking moieties. FIG. 6B provides synthesis routes of SOD-POx conjugates.

Figure 7A:
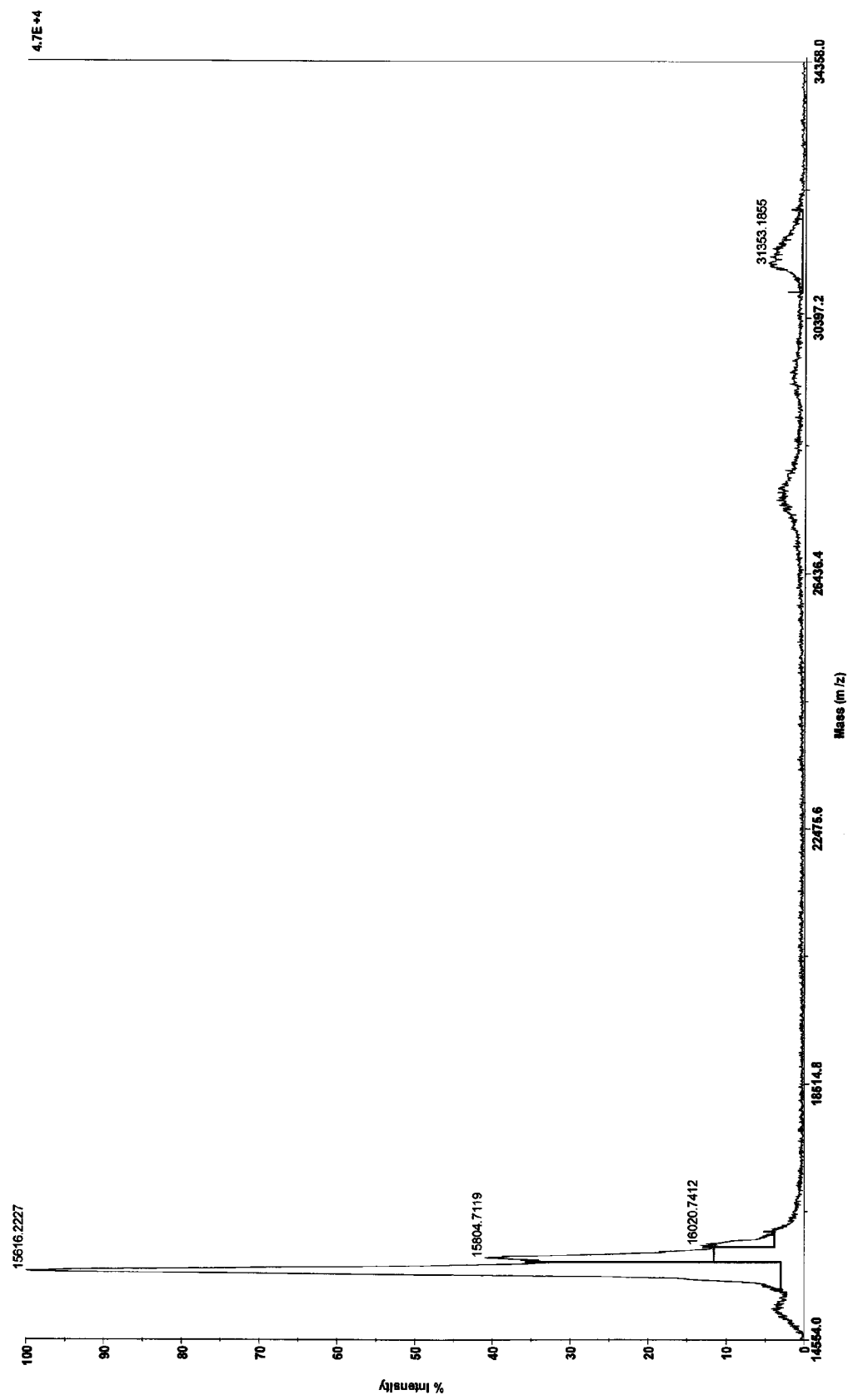
Figure 7B:
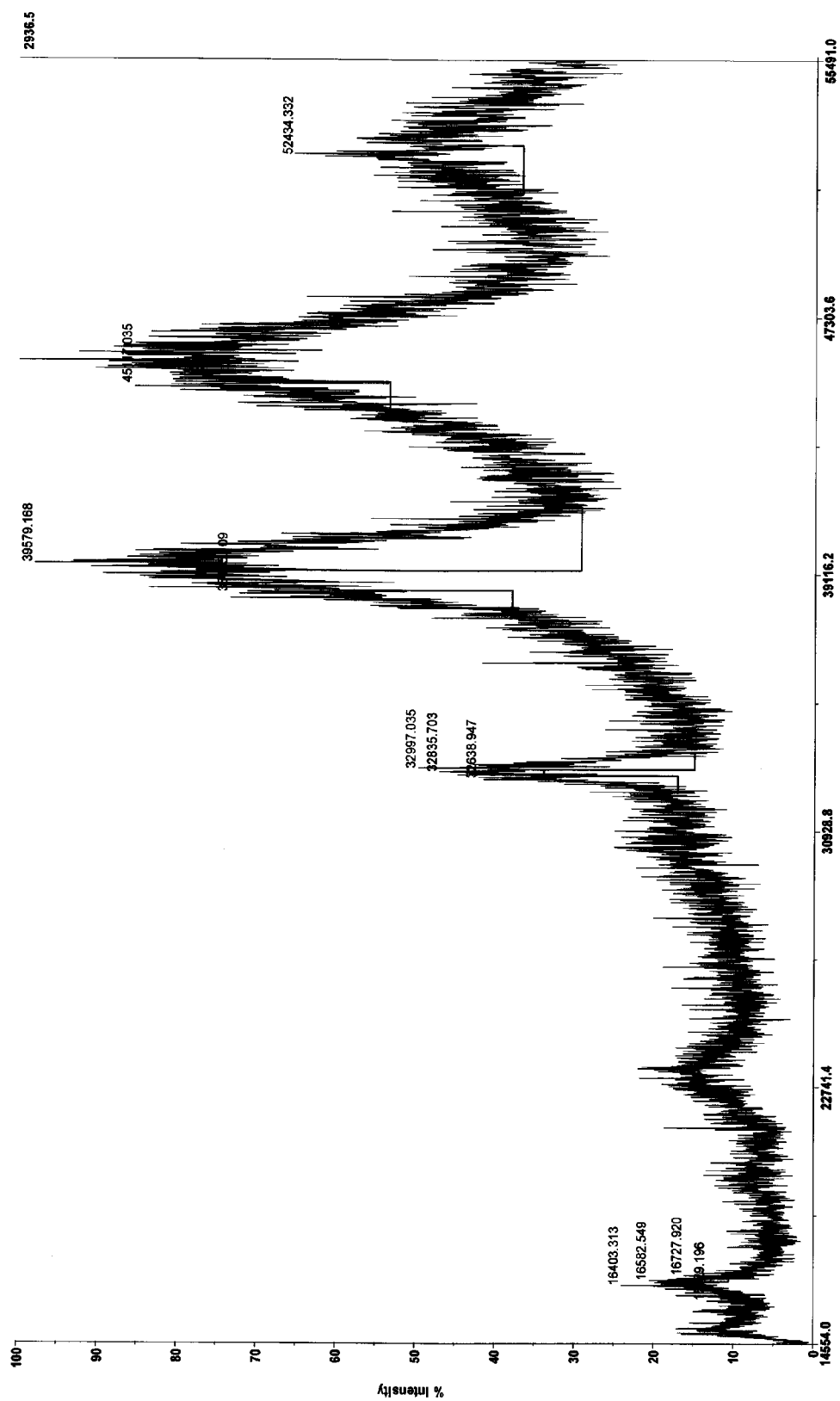
Figure 7C:
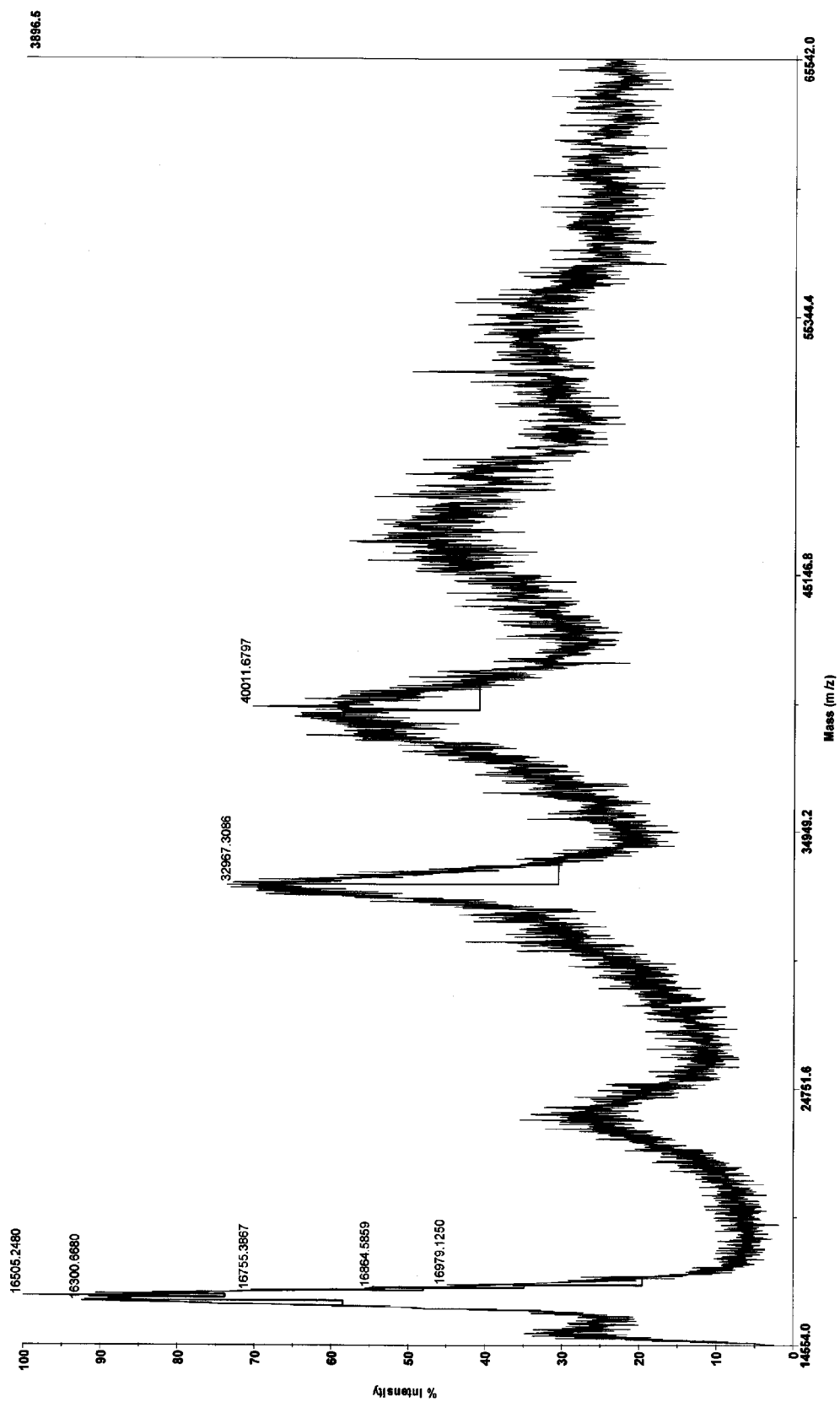

FIG. 7 provides mass spectra of SOD (FIG. 7A); SOD-P(MeOx-b-BuOx) (FIG. 7B); and SOD-P(EtOx-b-BuOx) (FIG. 7C).

Figure 8A:
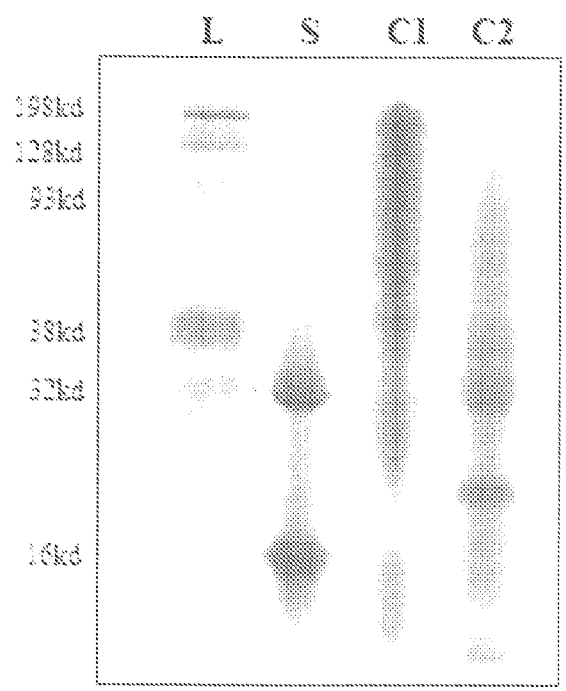
Figure 8B:
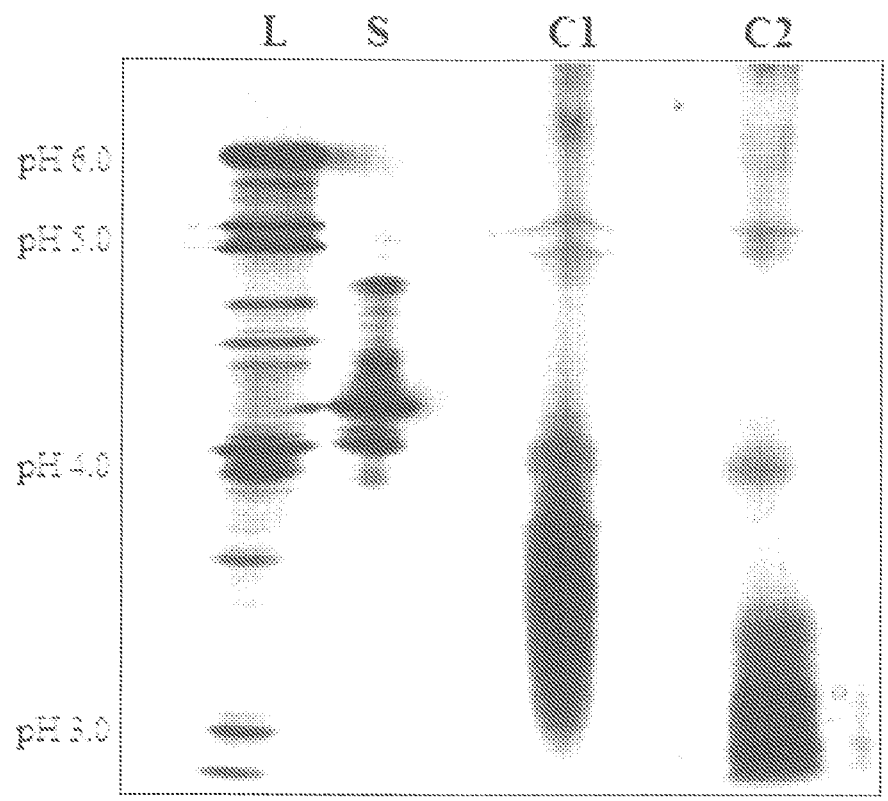

FIG. 8 provides images of a PAGE (FIG. 8A) and IEF (FIG. 8B) analysis of SOD and SOD-Pox. L—Ladder;

S—SOD; C1—SOD-P(MeOx-b-BuOx) conjugate; C2—SOD-P(EtOx-b-BuOx) conjugate.

Figure 9:
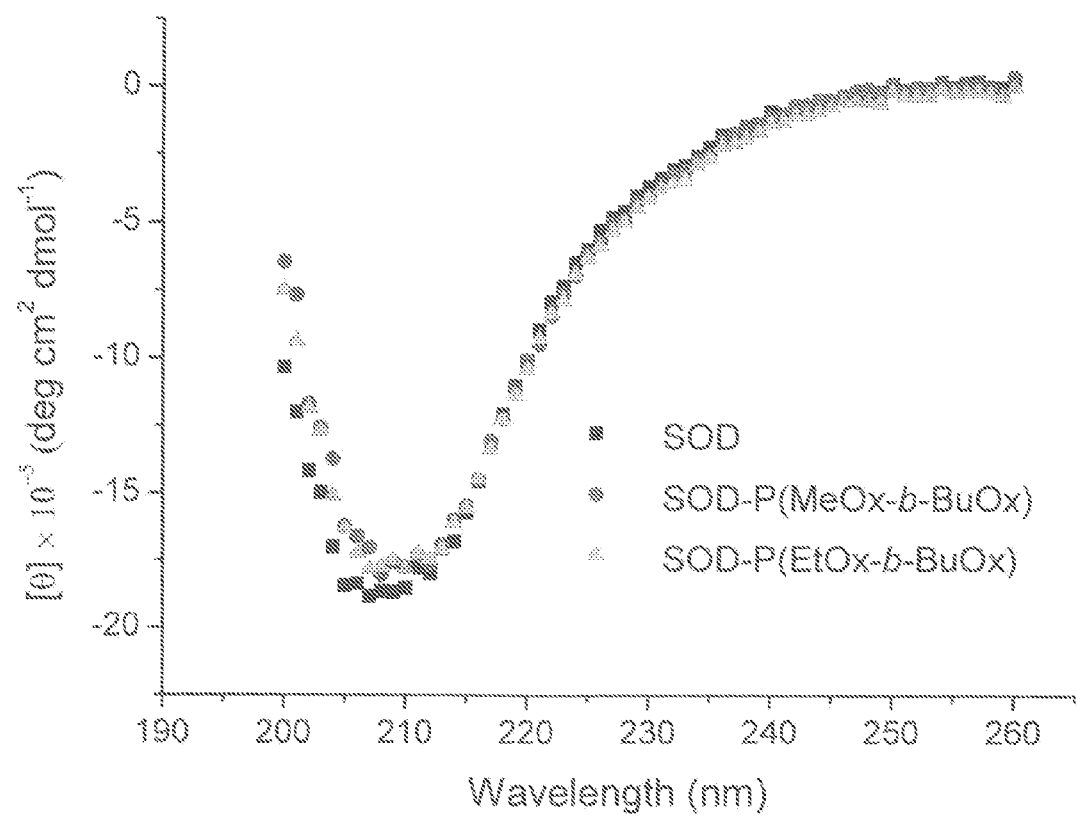

FIG. 9 provides the far-UV CD spectra of SOD and SOD-POx conjugates (200-260 nm).

Figure 10:
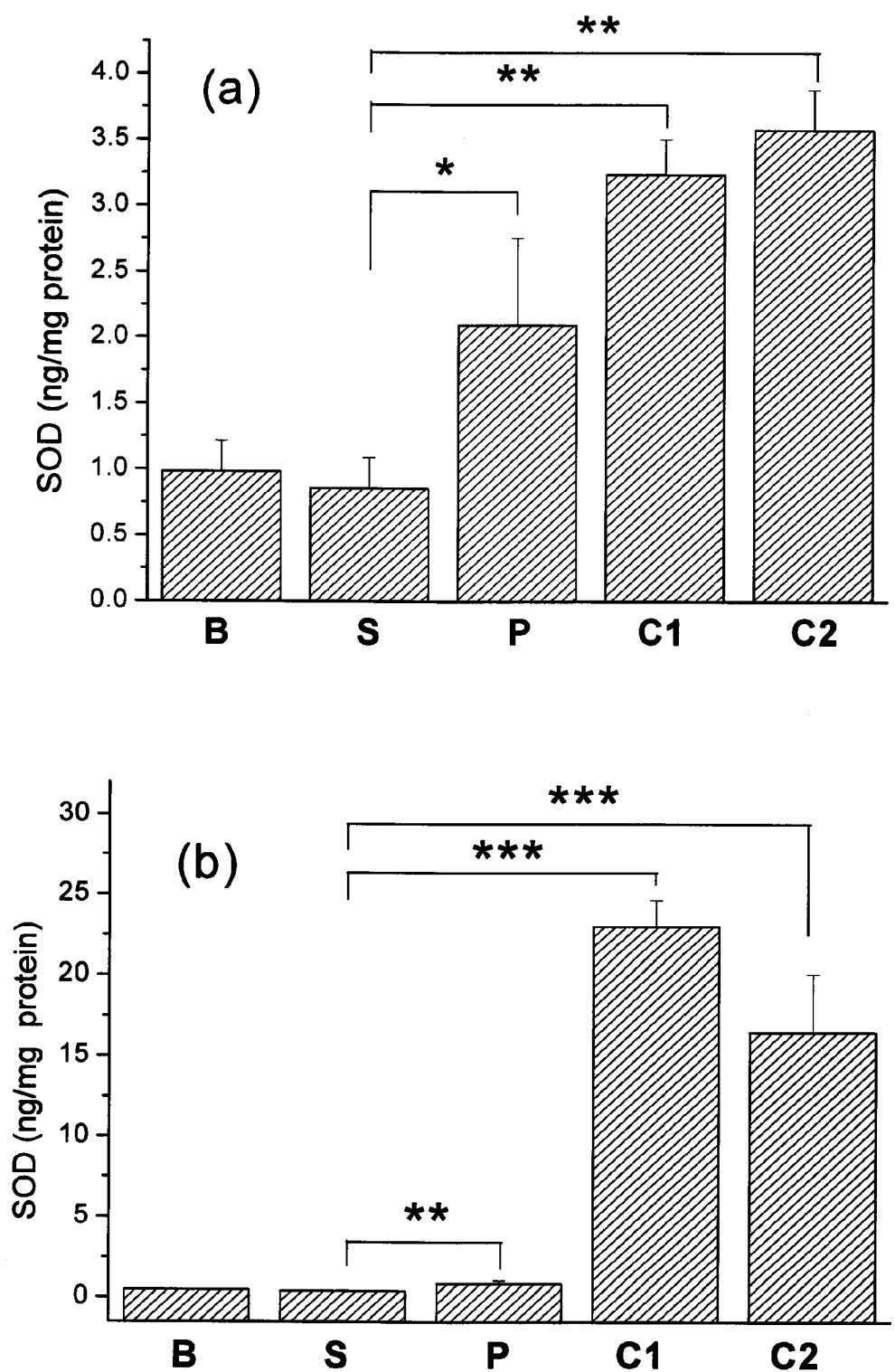

FIG. 10 provides graphs showing the cellular uptake of SOD, SOD-PEG and SOD-POx in MDCK cells (FIG. 10A) and CATH.a neuronal cells (FIG. 10B). B—Blank; S—SOD; P—SOD-PEG; C1—SOD-P(MeOx-b-BuOx); C2—SOD-P(EOx-b-BuOx). Data presented as means±SEM (n=4). Statistical analysis was done using one-way ANOVA: *p<0.05, p<0.01, *p<0.001.

DETAILED DESCRIPTION OF THE INVENTION

Recently poly(2-oxazoline)s have attracted attention for a variety of biomedical applications (Adams et al. (2007) Adv. Drug. Deliv. Rev., 59:1504-1520). Poly(2-ethyl-2-oxazoline) (PEtOx) and poly(2-methyl-2-oxazoline) (PMeOx) have shown similar properties as poly(ethylene glycol) (PEG), such as stealth (Zalipsky et al. (1996) J. Pharm. Sci., 85:133-137; Woodle et al. (1994) Bioconjug. Chem., 5:494-496), protein repellent (Konradi et al. (2008) Langmuir 24:613-616) and rapid renal clearance (Mero et al. (2008) J. Control Release, 125:87-95). Catalase (Miyamoto et al. (1990) Macromolecules 23:3201-3205), protein C (Velander et al. (1992) Biotech. Bioeng., 39:1024-1030.), trypsin (Mero et al. (2008) J. Control Release, 125:87-95) and various other proteins have been conjugated to PMeOx and PEtOx successfully. In certain cases, similar performance to PEGylated proteins has been reported. Non-covalent incorporation of proteins into POx micelles formed from amphiphilic block copolymers has also been described showing that a higher catalytic activity of proteins can be achieved by this method, both in aqueous and non-aqueous systems (Naka et al. (1994) Polymer J., 26:243-249). Herein, the conjugation of proteins with poly(2-oxazoline) copolymers is reported and the effects of such modification on the cellular uptake of the protein is evaluated. With 2-butyl-2-oxazoline (BuOx) as the hydrophobic monomer, two amphiphilic block copolymers P(MeOx-b-BuOx) and P(EtOx-b-BuOx), one random copolymer P(EtOx-co-BuOx) and one homopolymer PMeOx were selected and conjugated with proteins such as HRP and SOD. These conjugates were characterized in different ways and their cellular uptake (e.g., in MDCK and Caco-2 cells) were quantitively compared.

Several homo, random, and block copoly(2-oxazoline)s were synthesized and conjugated to proteins (e.g., horseradish peroxidase (HRP)) using biodegradable and non-biodegradable linkers. The HRP-poly(2-oxazoline) conjugates (HRP×POx) were characterized by amino group titration, SDS-PAGE, isoelectric focusing, enzymatic activity assay and conformation analysis. The conjugates contained average from one to two polymer chains per enzyme and 70%-90% of enzymatic activity was retained in most cases. Circular dichroic analysis revealed that polymer conjugation had effects on the secondary structure of apoprotein but the tertiary structure and heme environment were well maintained. Enhanced cellular uptake was found in the conjugates of two block copolymers (e.g., with MDCK cells and Caco-2 cells). Notably, the conjugates of random copolymer were less efficiently taken up by cells, but still more so than homopolymer conjugates. Conjugation with a block copolymer of 2-methyl-2-oxazoline and 2-butyl-2-oxazoline (HRP×P(MeOx-b-BuOx)) had the highest cellular uptake as compared to other conjugates. The data indicates that poly (2-oxazoline) modification has enhanced cellular delivery of proteins.

Only a quite limited number of types of polymers are widely recognized as suitable for a wide range of biomedical materials. Problems with these polymers include a lack of chemical and structural versatility and definition. Poly(2-oxazoline)s are a very valuable novel alternative for biomedical materials in general and as drug carriers in particular. The defined cationic ring opening polymerization reaction and chemical versatility of poly(2-oxazoline)s allows for very exact tuning of their solubility, their thermal responsiveness (LOST), and their aggregation behavior in aqueous solutions. Depending on the side chain, poly(2-oxazoline)s or poly(2-oxazoline) blocks can be extremely hydrophilic, amphiphilic, hydrophobic, or fluorophilic. Additionally, a wide range of side chain moieties have been introduced, including carboxylic acids, amines, aldehydes, alkanes, alkynes and thiols. These allow a wide range of specific coupling reactions (chemo-selective ligations) with bioactive compounds, e.g. peptides or drugs. In addition, multi-block, star-like, and star-like block copolymers may be synthesized.

Highly water soluble, well-defined poly(2-methyl-2-oxazoline) and poly(2-ethyl-2-oxazoline) polymers have been shown to not undergo unspecific accumulation in a host and the polymers are very rapidly excreted via the kidneys in the mouse. Furthermore, no cytotoxicity in various cell types of human, canine, and murine origin has been generally observed, even at very high concentrations of up to 20 mg/mL. Indeed, the polymers described in this invention are not known to be toxic or hazardous in any way in a relevant concentration range. In conclusion, the structural and chemical versatility of poly(2-oxazoline)s, together with their excellent biocompatibility, make this class of polymer ideal for delivering drugs and biomaterials.

I. Definitions

The following definitions are provided to facilitate an understanding of the present invention:

As used herein, the term "lipophilic" refers to the ability to dissolve in lipids. "Hydrophobic" designates a preference for apolar environments (e.g., a hydrophobic substance or moiety is more readily dissolved in or wetted by non-polar solvents, such as hydrocarbons, than by water).

As used herein, the term "hydrophilic" means the ability to dissolve in water.

As used herein, the term "amphiphilic" means the ability to dissolve in both water and lipids/apolar environments. Typically, an amphiphilic compound comprises a hydrophilic portion and a lipophilic (hydrophobic) portion.

As used herein, the term "biocompatible" refers to a substance which produces no significant untoward effects when applied to, or administered to, a given organism.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

"Polypeptide" and "protein" are sometimes used interchangeably herein and indicate a molecular chain of amino acids. The term polypeptide encompasses peptides, oligopeptides, and proteins. The terms also include post-expression modifications of the polypeptide, for example, glycosylations, acetylations, phosphorylations and the like. In addition, protein fragments, analogs, mutated or variant proteins, fusion proteins and the like are included within the meaning of polypeptide.

The term "isolated" may refer to protein, nucleic acid, compound, or cell that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), bulking substance (e.g., lactose, mannitol), excipient, auxiliary agent, filler, disintegrant, lubricating agent, binder, stabilizer, preservative or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. The compositions can be incorporated into particulate preparations of polymeric compounds such as polylactic acid, polyglycolic acid, etc., or into liposomes or micelles. Such compositions may influence the physical state, stability, rate of in vivo release, and rate of in vivo clearance of components of a pharmaceutical composition of the present invention. The pharmaceutical composition of the present invention can be prepared, for example, in liquid form, or can be in dried powder form (e.g., lyophilized). Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients (3rd Ed.), American Pharmaceutical Association, Washington, 1999.

The term "alkyl," as employed herein, includes both straight and branched chain hydrocarbons containing about 1 to about 50 carbons, about 1 to about 20, about 1 to about 15, or about 1 to about 10 carbons in the main chain. The hydrocarbon chain may be saturated or unsaturated (i.e., comprise double and/or triple bonds (alkenyl)). The hydrocarbon chain may also be cyclic or comprise a portion which is cyclic. The hydrocarbon chain of the alkyl groups may be interrupted with heteroatoms such as oxygen, nitrogen, or sulfur atoms. Each alkyl group may optionally be substituted with substituents which include, for example, alkyl, halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C(=O)$— or $NHRC(=O)$—, wherein R is an alkyl), urea (—$NHCONH_2$), alkylurea, aryl, ether, ester, thioester, nitrile, nitro, amide, carbonyl, carboxylate and thiol. Examples of simple alkyls include, without limitation, propyl, butyl, pentyl, hexyl, heptyl, octyl and nonyl.

The term "aryl," as employed herein, refers to monocyclic and bicyclic aromatic groups containing 6 to 10 carbons in the ring portion. Aryl groups may be optionally substituted through available carbon atoms. The aromatic ring system may include heteroatoms such as sulfur, oxygen, or nitrogen.

As used herein, the term "substantially cleaved" refers to the cleavage of the amphiphilic polymer from the compound of interest of the conjugates of the instant invention, particularly at the linker moiety. "Substantial cleavage" occurs when at least 50% of the conjugates are cleaved, preferably at least 75% of the conjugates are cleaved, more preferably at least 90% of the conjugates are cleaved, and most preferably at least 95% of the conjugates are cleaved.

As used herein, the term "biodegradable" or "biodegradation" is defined as the conversion of materials into less complex intermediates or end products by solubilization hydrolysis under physiological conditions, or by the action of biologically formed entities which can be enzymes or other products of the organism. The term "non-degradable" refers to a chemical structure that cannot be significantly cleaved under physiological conditions.

A "diagnostic agent" refers to a compound that may be used to detect, image and/or monitor the presence and/or progression of a condition(s), pathological disorder(s) and/or disease(s). A diagnostic agent may be any agent which may be used in connection with methods for imaging an internal region of the patient and/or diagnosing the presence or absence of a disease or disorder in the patient. Exemplary diagnostic agents include, for example, contrast agents for use in connection with ultrasound imaging, magnetic resonance imaging (MRI), or computed tomography (CT) imaging of the patient. Non-limiting examples of diagnostic agents include antibodies, antibody fragments, or other proteins, including those conjugated to a detectable agent. As used herein, the term "detectable agents" refer to any molecule, compound and/or substance that is detectable by any methodology available to one of skill in the art. Non-limiting examples of detectable agents include dyes (e.g., fluorescent), metals, isotopes, or radioisotopes. Diagnostic agents may also include any other agents useful in facilitating diagnosis of a disease or other condition in a patient, whether or not an imaging methodology is employed.

II. Polymer

In a preferred embodiment of the instant invention, the synthetic polymers of the instant invention are amphiphilic copolymers (e.g., random copolymers, block copolymers, and the like). In a particular embodiment, the synthetic polymers are amphiphilic block copolymers which comprise at least one hydrophilic polymer segment and at least one hydrophobic (lipophilic) polymer segment. Block copolymers are most simply defined as conjugates of at least two different polymer segments (Tirrel, M. In: Interactions of Surfactants with Polymers and Proteins. Goddard E. D. and Ananthapadmanabhan, K. P. (eds.), CRC Press, Boca Raton, Ann Arbor, London, Tokyo, pp. 59-122, 1992). The simplest block copolymer architecture contains two segments joined at their termini to give an A-B type diblock. Consequent conjugation of more than two segments by their termini yields A-B-A type triblock, A-B-A-B-type multiblock, or even multisegment A-B-C-architectures. If a main chain in the block copolymer can be defined in which one or several repeating units are linked to different polymer segments, then the copolymer has a graft architecture of, e.g., an $A(B)_n$ type. More complex architectures include for example $(AB)_n$ or $A_nB_m$ starblocks which have more than two polymer segments linked to a single center. An exemplary block copolymer of the instant invention has the formula A-B or B-A, wherein A is a hydrophilic polymer segment and B is a hydrophobic polymer segment. Another exemplary block copolymer has the formula A-B-A. Block copolymers structures include, without limitation, linear copolymers, star-like block copolymers, graft block copolymers, dendrimer based copolymers, and hyperbranched (e.g., at least two points of branching) block copolymers. The segments of the block copolymer may have from about 2 to about 1000, about 2 to about 500, about 2 to about 300, or about 2 to about 100 repeating units or monomers.

Poly(2-oxazoline) block copolymers (also termed poly(N-acetylethylenimine)s) of the instant invention may be synthesized by the living cationic ring-opening polymerization of 2-oxazolines. The synthetic versatility of poly(2-oxazoline)s allows for a precise control over polymer termini and hydrophilic-lipophilic balance (HLB). Block length, structure, charge, and charge distribution of poly(2-oxazoline)s may be varied. For example, the size of the hydrophilic and/hydrophobic blocks may be altered, triblock polymers may be synthesized, star-like block copolymers may be used, polymer termini may be altered, and ionic side chains and/or ionic termini may also be incorporated. Ionic side chains (e.g., comprising —R—$NH_2$ or R—COOH, wherein R is an alkyl) may be incorporated into the hydrophilic (preferably) or hydrophobic block.

Poly(2-oxazoline)s (also known as 2-substituted 4,5-dihydro oxazoles) are polysoaps and depending on the residue at the 2-position of the monomer can be hydrophilic (e.g., methyl, ethyl) or hydrophobic (e.g. butyl, propyl, pentyl, nonyl, phenyl, and the like) polymers. Moreover, numerous monomers introducing pending functional groups are available (Taubmann et al. (2005) Macromol. Biosci., 5:603; Cesana et al. (2006) Macromol. Chem. Phys., 207:183; Luxenhofer et al. (2006) Macromol., 39:3509; Cesana et al. (2007) Macromol. Rapid Comm., 28:608). Poly(2-oxazoline)s can be obtained by living cationic ring-opening polymerization (CROP), resulting in well-defined block copolymers and telechelic polymers of narrow polydispersities (Nuyken, et al. (1996) Macromol. Chem. Phys., 197: 83; Persigehl et al. (2000) Macromol., 33:6977; Kotre et al. (2002) Macromol. Rapid Comm., 23:871; Fustin et al. (2007) Soft Matter, 3:79; Hoogenboom et al. (2007) Macromol., 40:2837). Several reports indicate that hydrophilic poly(2-oxazoline)s are essentially non-toxic and biocompatible (Goddard et al. (1989) J. Control. Release, 10:5; Woodle et al. (1994) Bioconjugate Chem., 5:493; Zalipsky et al. (1996) J. Pharm. Sci., 85:133; Lee et al. (2003) J. Control. Release, 89:437; Gaertner et al. (2007) J. Control. Release, 119:291). Using lipid triflates or pluritriflates, lipopolymers (Nuyken, et al. (1996) Macromol. Chem. Phys., 197:83; Persigehl et al. (2000) Macromol., 33:6977; Kotre et al. (2002) Macromol. Rapid Comm., 23:871; Fustin et al. (2007) Soft Matter, 3:79; Hoogenboom et al. (2007) Macromol., 40:2837; Punucker et al. (2007) Soft Matter, 3:333; Garg et al. (2007) Biophys. J., 92:1263; Punucker et al. (2007) Phys. Rev. Lett., 98:078102/1; Luedtke et al. (2005) Macromol. Biosci., 5:384; Punucker et al. (2005) J. Am. Chem. Soc., 127:1258) or star-like poly(2-oxazoline)s are readily accessible. Additionally, various poly(2-oxazoline)s with terminal quaternary amine groups have been reported, which interact strongly with bacterial cell membranes (Waschinski et al. (2005) Macromol. Biosci., 5:149; Waschinski et al. (2005) Biomacromol., 6:235).

In a particular embodiment, the biocompatible, water soluble copolymer of the instant invention comprises at least one hydrophilic block A and at least one hydrophobic block B. The at least one hydrophilic block A and at least one hydrophobic block B are attached through linkages which are stable or labile (e.g., biodegradable under physiological conditions (e.g., by the action of biologically formed entities which can be enzymes or other products of the organism)).

Although the hydrophilic block of the polymer preferably comprises at least one poly(2-oxazoline), the hydrophilic block may also comprise at least one polyethyleneoxide, polyester, or polyamino acid (e.g. poly(glutamic acid) or poly(aspartic acid)) or block thereof. The hydrophilic block of the polymer may comprise at least one hydrophilic poly(2-oxazoline). Examples of the hydrophilic polymer block include poly(2-oxazoline)s with hydrophilic substituents at the 2-position of the oxazoline ring. In a particular embodiment, the hydrophilic substituent is an alkyl. In another embodiment, the hydrophilic substituent comprises about 5 or fewer carbon atoms, particularly about 3 or fewer carbon atoms, or 2 or fewer carbons. Examples of hydrophilic poly(2-oxazoline)s include, without limitation, 2-methyl-2-oxazoline, 2-ethyl-2-oxazoline, and mixtures thereof.

The hydrophobic block of the polymer may comprise at least one hydrophobic poly(2-oxazoline). Examples of the hydrophobic polymer block include poly(2-oxazoline)s with hydrophobic substituents at the 2-position of the oxazoline ring. In a particular embodiment, the hydrophobic substituent is an alkyl or an aryl. In another embodiment, the hydrophobic substituent comprises 3 to about 50 carbon atoms, 3 to about 20 carbon atoms, 3 to about 12 carbon atoms, particularly 3 to about 6 carbon atoms, or 4 to about 6 carbons. In a particular embodiment, the hydrophobic block copolymer is 2-butyl-2-oxazoline, 2-propyl-2-oxazoline, 2-nonyl-2-oxazoline or mixtures thereof.

In a particular embodiment of the instant invention, the copolymer of the instant invention is represented by the formula:

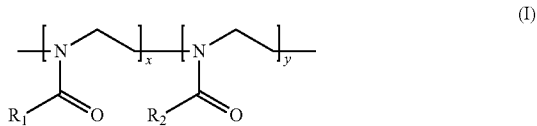

wherein x and y are independently selected between 1 or 2 and about 300, particularly about 5 to about 150, and more particularly about 10 to about 100; one of $R_1$ and $R_2$ is selected from the group consisting of —H, —OH, —$NH_2$, —SH, —$CH_3$, —$CH_2CH_3$, and an alkyl (hydrophilic; e.g. comprising 1 or 2 carbon atoms); and the other R group is an alkyl (hydrophobic; e.g., comprising 3 or more carbons) or an aryl. In a particular embodiment, x and y are independently 5 or more, 10 or more, or 20 or more, and particularly less than 300, less than 200, or less than 100. In a particular embodiment, for the hydrophilic block, R is selected from the group consisting of —CH$_3$ and —CH$_2$CH$_3$. In a particular embodiment, for the hydrophobic block, R is the formula (CH$_2$)$_n$—R$_3$, wherein R$_3$ is —OH, —COOH, —CHCH$_2$, —SH, —NH$_2$, —CCH, —CH$_3$, or —CHO and wherein n is about 2 to about 50, about 2 to about 20, about 2 to about 12, or about 3 to 6. In a particular embodiment, for the hydrophobic block, R comprises 3 to about 50 carbon atoms, 3 to about 20 carbon atoms, 3 to about 12 carbon atoms, or 3 to about 6 carbon atoms. In yet another embodiment, R is butyl (including isobutyl, sec-butyl, or tert-butyl) or propyl (including isopropyl). In yet another embodiment, R is —CH$_2$—CH$_2$—CH$_2$—CH$_3$ or —CH$_2$—CH$_2$—CH$_3$. In a particular embodiment, the polymer is selected from the those presented in FIG. 1.

Amphiphilic block copolymers can be obtained from hydrophilic 2-methyl-2-oxazoline (MeOx) and hydrophobic 2-nonyl-2-oxazoline (NonOx) (Bonne et al. (2004) Colloid Polym. Sci., 282:833; Bonne et al. (2007) Coll. Polym. Sci., 285:491). Various amphiphilic block copolymers (also additionally bearing carboxylic acid side chains for micellar catalysis (Zarka et al. (2003) Chem-Eur. J., 9:3228; Bortenschlager et al. (2005) J. Organomet. Chem., 690:6233; Rossbach et al. (2006) Angew. Chem. Int. Ed., 45:1309)) and lipopolymers have been reported and their aggregation behavior in aqueous solution was studied (Bonne et al. (2004) Colloid Polym. Sci., 282:833; Bonne et al. (2007) Coll. Polym. Sci., 285:491). CROP allows for an exact tuning of the hydrophilic-lipophilic balance (HLB) and initiation with a bi-functional initiator allows two step synthesis of triblock copolymers in contrast to the three step synthesis necessary when, e.g., methyltriflate is used as an initiator. This approach has the additional benefit that both polymer termini can be easily functionalized (e.g., with the same moiety).

The initiators used to generate the copolymers of the instant invention can be any initiator used in the art. Additionally, the termini of the copolymers of the instant invention can be any terminus known in the art. The polymers can be prepared from mono-, bi- or multifunctional initiators (such as multifunctional triflates or multifunctional oxazolines) such as, but not restricted to, methyltriflate, 1,2-bis (N-methlyoxazolinium triflate) ethane or pentaerithritol tetrakistriflate. In a particular embodiment, at least one termini comprises an amine (e.g., a secondary amine). Examples of polymer termini include, for example, —OH, —CH$_3$, —OCH$_3$,

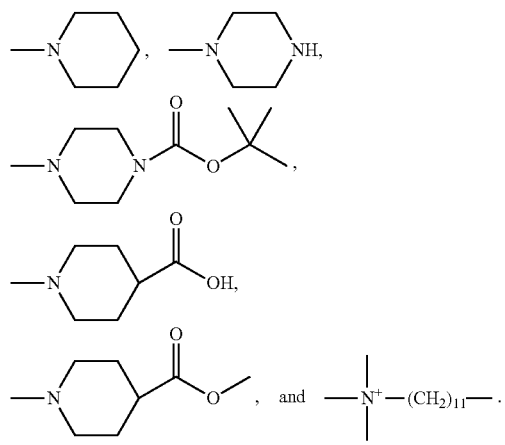

In a particular embodiment, at least one termini is a piperazine group.

Amphiphilic copolymers of the instant invention (e.g., piperazine terminated copolymers) may be additionally labeled with a fluorescent dye (e.g., fluorescein isothiocyanate, FITC) to allow evaluation of the localization of these polymers by confocal microscopy (Batrakova et al. (2001) J. Pharmacol. Exp. Ther., 299:483; Bonne et al. (2004) Colloid Polym. Sci., 282:833; Bonne et al. (2007) Coll. Polym. Sci., 285:491).

The instant invention also encompasses compositions comprising at least one of the polymer and/or polymer conjugates of the instant invention and at least one pharmaceutically acceptable carrier. The composition may further comprise at least one bioactive agent (e.g. therapeutic agent and/or diagnostic agent) as set forth below. The composition may further comprise at least one cosmetic agent.

III. Bioactive and Therapeutic Agents

The polymers of the instant invention may be used to deliver any agent(s) or compound(s) (e.g., small molecules), particularly bioactive agents (e.g., therapeutic agent or diagnostic agent) to a cell(s), tissue, or subject (including non-human animals). The polymers of the instant invention may also be used to cosmetic agent(s) to a cell(s), tissue, or subject (including non-human animals). As used herein, the term "bioactive agent" also includes compounds to be screened as potential leads in the development of drugs or therapeutic agents. Indeed, the instant invention encompasses methods for the detection of active compounds which interact with a target of interest in a screening test comprising incorporating an active compound into a composition of the instant invention and subjecting the composition to the screening test.

The bioactive agent, particularly therapeutic agents, of the instant invention include, without limitation, polypeptides, peptides, glycoproteins, nucleic acids, synthetic and natural drugs, peptoides, polyenes, macrocyles, glycosides, terpenes, terpenoids, aliphatic and aromatic compounds, and their derivatives. In a particular embodiment, the agent conjugated to the polymer is a polypeptide. In another embodiment, the therapeutic agent effects amelioration and/ or cure of a disease, disorder, pathology, and/or the symptoms associated therewith. The polymers of the instant invention may be operably linked to one or more agent. The agent of the instant invention may be operably linked to more than one polymer.

Suitable drugs include, without limitation, those presented in Goodman and Gilman's The Pharmacological Basis of Therapeutics (11th Ed.) or The Merck Index (14th Ed.). Genera of drugs include, without limitation, drugs acting at synaptic and neuroeffector junctional sites, drugs acting on the central nervous system, drugs that influence inflammatory responses, drugs that affect the composition of body fluids, drugs affecting renal function and electrolyte metabolism, cardiovascular drugs, drugs affecting gastrointestinal function, drugs affecting uterine motility, chemotherapeutic agents e.g., for cancer, for parasitic infections, and for microbial diseases), antineoplastic agents, immunosuppressive agents, drugs affecting the blood and blood-forming organs, hormones and hormone antagonists, dermatological agents, heavy metal antagonists, vitamins and nutrients, vaccines, oligonucleotides and gene therapies. Examples of drugs suitable for use in the present invention include, without limitation, testosterone, testosterone enanthate, testosterone cypionate, methyltestosterone, amphotericin B, nifedipine, griseofulvin, taxanes (including, without limitation, paclitaxel, docetaxel, larotaxel, ortataxel, tesetaxel and the like), doxorubicin, daunomycin, indomethacin, ibuprofen, etoposide, cyclosporin A, vitamin E, and testosterone. In a particular embodiment, the drug is nifedipine, griseofulvin, a taxane, amphotericin B, etoposide or cyclosporin A.

In a particular embodiment, the agent being delivered is a cosmetic agent. As used herein, a "cosmetic agent" refers to a substance suitable for topical administration (e.g., skin, hair, and/or nails) for aesthetic purposes. The term "cosmetic agent" may refer to any agent, such as a pigment or fragrance, which may be dermally or topically applied (e.g., to skin, hair, or nails) for aesthetic effect (e.g., improving the skin surface) and which preferably does not cause irritation. Cosmetic agents are well known in the art. Improving the skin surface of the mammal (e.g., human) can include, e.g., any one or more of the following: (1) diminishing the presence of, preventing, improving the appearance of and/or treating wrinkles and/or fine lines present on a skin surface; (2) exfoliating the skin surface; (3) firming the skin surface; and (4) hydrating the skin surface. Suitable cosmetic agents include, without limitation, coloring agents, fragrances, vitamins (e.g., vitamin A, vitamin B, vitamin C, and vitamin E), essential amino acids, and essential fatty acids, antioxidants (e.g., free radical scavengers, alpha hydroxy acids (e.g., lactic acid, tartaric acid, citric acid, glycolic acid, malic acid, alpha-hydroxy octanoic acid, alpha-hydroxy caprylic acid, mixed fruit acids, sugar cane extracts), beta hydroxy acids (e.g., salicylic acid, beta-hydroxybutanoic acid, tropic acid, trethocanic acid), Vitamin C, Vitamin E, Vitamin A, lycopene, tumeric, green tea, white tea, and acceptable salts thereof), collagen synthesis stimulators (e.g., plant extracts containing kinetin (furfurylaminopurine), Vitamin C, copper containing peptides), fibroblast growth stimulators (e.g., copper containing peptides, retin A, cytokines (e.g., fibroblast growth factors)), collagen cross-linking inhibitors (e.g., aminoguanidine, carnosine), caffeine, theophyline, anti-aging agents (sunscreens, anti-oxidants (e.g., vitamins such as ascorbic acid, vitamin B, biotin, pantothenic acid, vitamin D, vitamin E and vitamin C), sodium bisulfite, yeast extract, gingko biloba, bisabolol, panthenol, alpha hydroxy acids, and oligosaccharides (e.g., melibiose)), steroids, anti-inflammatory agents (e.g., steroidal (e.g., corticosteroids (e.g., hydrocortisone), hydroxyltriamcinolone, alpha-methyl dexamethasone, dexamethasone-phosphate, beclomethasone dipropionate, clobetasol valerate, desonide, desoxycorticosterone acetate, dexamethoasone, dichlorisone, deflorasonediacetate, diflucortolone valerate, fluadronolone, fluclarolone acetonide, fludrocortisone, flumethasone pivalate, fluosinolone acetonide, fluocionide, flucortine butylester, fluocortolone, flupredidene (flupredylidene)acetate, flurandronolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone and its esters, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, and triamcinolone) and non-steroidal anti-inflammatory agents (e.g., salicylates, acetic acid derivatives, fenamates, propionic acid derivatives and pyrazoles)), pigment modulating agents (e.g., depigmenting agents such as lipoic acid, arbutim, dihydrolipoic acid, resveratrol, ascorbic acid, kojic acid, hydroquinone, isoflavones, retinoids (e.g., retinol, retinoic acid, and retinyl palmitate), tyrosinase inhibitors, melanosome transfer inhibitors, selective cytotoxic agents for melanocytes, and natural extracts (e.g., licorice extract, gatuline A (pilewort extract), and micromerol (butylene glycol and apple extract))), exfoliating agents (e.g., organic hydroxy acids (e.g., alpha and beta hydroxy acids), salicylic acid, glycolic acid, lactic acid, 5-octanoyl salicylic acid, hydroxyoctanoic acid, hydroxycaprylic acid, lanolin fatty acids, sulphydryl compounds, protease or peptase enzymes (natural and bioengineered), mimetic compounds that mimic hydroxyl acids, and bioactive metals (e.g., manganese, tin, and copper), and natural soy-based products), lipid molecules (e.g., sphingosine-1-phosphate and lysophosphatidic acid), amino acids (e.g., arginine and lysine), vitamin A, vitamin D, bradykinins, substance P, calcium gene-related peptide (CGRP), insulin, vascular endothelial growth factor (VEGF), thrombin, antibodies to platelet endothelial cells surface marker, extra-cellular matrix proteins (e.g., glycosaminoglycans), fibrous proteins (e.g., collagen; elastin, fibronectins, and laminin), growth factors (e.g., platelet derived growth factors (PDGF), epidertnal growth factor (EGF), keratinocyte growth factor (KGF), vascular endothelial growth factors (VEGFs), fibroblast growth factors (FGFs), transforming growth factors (TGFs), and insulin-like growth factor-1 (IGF-1)) tumor necrosis factor-alpha (TNF-alpha), tumor necrosis factor-beta (TNF-beta), and thymosin B4), anti-cellulite agents (e.g., xanthine compounds such as caffeine, theophylline, theobromine, and aminophylline), moisturizing agents (e.g., polyhydric alcohols (e.g., glycerin, propylene glycol, 1,3-buthyleneglycol, polyethylene glycol, sorbitol, isoprene glycol, and POB methyl glucoside), anti-swelling agents (e.g., lanolin, aloe vera extract, hydrocortisone, and menthol), and combinations thereof.

In a particular embodiment of the instant invention, polypeptides, peptides, or proteins are conjugated to the amphiphilic polymers of the instant invention (e.g., in order to mediate crossing of a biological membrane). In a particular embodiment of the instant invention, the polypeptides conjugated to the amphiphilic polymers are therapeutic proteins, i.e., they effect amelioration and/or cure of a disease, disorder, pathology, and/or the symptoms associated therewith. The polypeptides may have therapeutic value against, without limitation, neurological degenerative disorders, stroke, Alzheimer's disease, Parkinson's disease, Huntington's disease, trauma, infections, meningitis, encephalitis, gliomas, cancers (including brain metastasis), HIV, HIV associated dementia, HIV associated neurocognitive disorders, paralysis, amyotrophic lateral sclerosis, CNS-associated cardiovascular disease, prion disease, obesity, metabolic disorders, inflammatory disease, and lysosomal diseases (such as, without limitation, Pompe disease, Niemann-Pick, Hunter syndrome (MPS II), Mucopolysaccharidosis I (MPS I), GM2-gangliosidoses, Gaucher disease, Sanfilippo syndrome (MPS IIIA), and Fabry disease). Examples of specific polypeptides include, without limitation, antibodies, antibody fragments, leptin (to treat obesity), cytokines, enkephalin, growth factors (e.g., epidermal growth factor (EGF), basic fibroblast growth factor (bFGF), nerve growth factor (NGF)), amyloid beta binders (e.g. antibodies), modulators of $\alpha$-, $\beta$-, and/or $\gamma$-secretases, Glial-derived neutrotrophic factor (GDNF), vasoactive intestinal peptide, acid alpha-glucosidase (GAA), acid sphingomyelinase, iduronate-2-sultatase (I2S), $\alpha$-L-iduronidase (IDU), $\beta$-Hexosaminidase A (HexA), Acid $\beta$-glucocerebrosidase, N-acetylgalactosamine-4-sulfatase, α-galactosidase A, bone morphogenic proteins, drug resistance proteins, toxoids, erythropoietins, proteins of the blood clotting cascade (e.g., Factor VII, Factor VIII, Factor IX, Factor X, etc.), subtilisin, ovalbumin, alpha-1-antitrypsin (AAT), DNase, superoxide dismutase (SOD), lysozymes, ribonucleases, hyaluronidase, collagenase, human growth hormone (hGH), erythropoietin (EPO), insulin, insulin-like growth factors, interferons (e.g., IFN-alpha), glatiramer, granulocyte-macrophage colony-stimulating factor (GMCSF), granulocyte colony-stimulating factor (GCSF), desmopressin, hirudin, leutinizing hormone release hormone (LHRH) agonists (e.g., leuprolide, goserelin, buserelin, gonadorelin, histrelin, nafarelin, deslorelin, fertirelin, triptorelin), LHRH antagonists, vasopressin, cyclosporine, calcitonin, parathyroid hormone, parathyroid hormone peptides, glucogen-like peptides, and analogs thereof. Certain of the polypeptides are exemplified in Table 5.

therapeutic polypeptide does not produce its intended therapeutic effect. In this embodiment, the therapeutic polypeptide may be linked to the polymer via a biodegradable (cleavable) linker.

In a particular embodiment, the polypeptide is superoxide dismutase (SOD) (e.g., SOD1, also called Cu/Zn SOD). In a particular embodiment, SOD is linked to the polymer via a non-degradable linker (e.g., the remainder from conjugating with DSS) or a degradable linker (e.g., disulfide containing linkers such as the remainder from conjugating with DSP). The polymer conjugated SOD may be administered to a subject (e.g., in a composition comprising at least one pharmaceutically acceptable carrier) as an antioxidant therapy. The polymer conjugated SOD may also be administered to a subject (e.g., in a composition comprising at least one pharmaceutically acceptable carrier) in order to treat inflammation, neurodegeneration, neurological disorders and other disorders of the central nervous system (including,

TABLE 5

| Protein | Ref. | Disease | Function |
|---|---|---|---|
| Glial-derived neutrotrophic factor (GDNF) | Schapira, A. H. (2003) Neurology 61: S56-63 | Parkinson's and Alzheimer's diseases Stroke | Neuroprotection and neurorestoration |
| Epidermal growth factor (EGF) | Ferrari, G., et al. (1990) Adv Exp Med Biol. 265: 93-99 | Parkinson's and Alzheimer's diseases Stroke | Stimulates dopaminergic development |
| Basic fibroblast growth factor (bFGF) | Ferrari, G., et al. (1991) J Neurosci Res. 30: 493-497 | Parkinson's and Alzheimer's diseases Stroke | Stimulates proliferation and migration of neutral stem cells |
| Nerve growth factor (NGF) | Koliatsos, V. E., et al. (1991) Ann Neurol. 30: 831-840 | Parkinson's and Alzheimer's diseases Stroke | Protects cholinergic cells from injury-induced death |
| Vasoactive intestinal peptide | Dogrukol-Ak, D., et al. (2003) Peptides 24: 437-444 | Alzheimer's diseases Stroke | Promote neuronal survival, prevent exitotoxic cell death |
| Acid alpha-glucosidase (GAA) | Amalfitano, A., et al. (2001) Genet Med. 3: 132-138 | Pompe (lysosomal disease) | Enzyme replacement therapy |
| Acid sphingomyelinase | Simonaro, C. M., et al. (2002) Am J Hum Genet. 71: 1413-1419 | Niemann-Pick (lysosomal disease) | Enzyme replacement therapy |
| Iduronate-2-sultatase (I2S) | Muenzer, J., et al. (2002) Acta Paediatr Suppl. 91: 98-99 | Hunter syndrome (MPS II) (lysosomal disease) | Enzyme replacement therapy |
| α-L-iduronidase (IDU) | Wraith, J. E., et al. (2004) J Pediatr. 144: 581-588 | Mucopolysaccharidosis I (MPS I) (lysosomal disease) | Enzyme replacement therapy |
| β-Hexosaminidase A (HexA) | Wicklow, B. A., et al. (2004) Am J Med Genet. 127A: 158-166 | GM2-gangliosidoses (lysosomal disease) | Enzyme replacement therapy |
| Acid β-glucocerebrosidase | Grabowski, G. A., (2004) J Pediatr. 144: S15-19. | Gaucher disease (lysosomal disease) | Enzyme replacement therapy |
| N-acetylgalactosamine-4-sulfatase | Auclair, D., et al. (2003) Mol Genet Metab. 78: 163-174 | Sanfilippo syndrome (MPS IIIA) (lysosomal disease) | Enzyme replacement therapy |
| α-galactosidase A | Przybylska, M., et al. (2004) J Gene Med. 6: 85-92 | Fabry (lysosomal disease) | Enzyme replacement therapy |

In a particular embodiment, the therapeutic polypeptide exhibits therapeutic activity without cleavage of the polymer from the protein (i.e., the conjugation of the polymer to the polypeptide does not significantly decrease the activity of the polypeptide. In another embodiment, the therapeutic polypeptide does not exhibit any appreciable therapeutic activity prior to cleavage/removal of the linker and/or amphiphilic polymer. In other words, prior to cleavage the but not limited to, Alzheimer's disease, Parkinson's disease, neurocardiovascular disease/dysregulation) as well as for immune enhancement and as an anti-aging agent. In a particular embodiment, the polymer conjugated SOD is administered to a subject in need thereof to treat a neurodegenerative disease (e.g., Alzheimer's disease, Parkinson's disease, Lewy Body disease, amyotrophic lateral sclerosis, and prion disease). In a particular embodiment, the disease is stroke, traumatic brain injury, hypertension (including in chronic heart failure), or obesity.

The compound of interest is operably linked (e.g., non-covalently or covalently) to the polymer of the instant invention. In a particular embodiment, the compound of interest is covalently linked (e.g., directly or via a linker) to the polymer of the instant invention. The linker may be degradable (cleavable) or non-degradable. In a particular embodiment, the cleavable linker comprises a disulfide bond. The cleavable linker may comprise a recognition site for a protease. Exemplary proteases include, without limitation, trypsin, endosomal cathepsins, cathepsin B, lysosomal proteases, and colagenase. In a particular embodiment, the compound of interest is linked to the polymer via a non-degradable linker (e.g., the remainder from conjugating with disuccinimidyl suberate (DSS)) or a degradable linker (e.g., disulfide containing linkers such as the remainder from conjugating with dithiobis(succinimidyl propionate) (DSP)).

The linker moiety joining the amphiphilic polymer and the protein of the conjugate may be non-biodegradable or biodegradable. In a particular embodiment, the linker is cleaved upon entry into a cell or upon crossing a histohematic barrier or blood brain barrier (BBB). As stated above, the linker moiety may comprise amino acids that constitute a protease recognition site or other such specifically recognized enzymatic cleavage site. Exemplary protease recognition sites include, without limitation, amino acid sequences cleavable by endosomal cathepsin, such as cathepsin B (e.g., Gly-(Phe)-Leu-Gly; see, e.g., DeNardo et al. (2003) Clinical Cancer Res. 9:3865s-72s); sequences cleavable by lysosomal proteases (e.g., Gly-Leu-Gly and Gly-Phe-Leu-Gly; see, e.g., Guu et al. (2002) J. Biomater. Sci. Polym. Ed. 13:1135-51; Rejmanova et al. (1985) Biomaterials 6:45-48); and sequences cleavable by collagenase (e.g., GGGLGPAGGK and KALGQPQ; see, e.g., Gobin and West (2003) Biotechnol. Prog. 19:1781-5; Kim and Healy (2003) Biomacromolecules 4:1214-23).

In another embodiment, the linker region comprises a disulfide bond. In a particular embodiment, the disulfide bond is stable in the blood, but hydrolyzable by reductases (e.g., those present in the BBB). Representative examples of linker moieties comprising a disulfide bond include, without limitation:

—OC(O)NH(CH$_2$)$_2$NHC(O)(CH$_2$)$_2$SS(CH$_2$)$_2$C(O)NH—;

—OC(O)NH(CH$_2$)$_2$SS(CH$_2$)$_2$N=CH—; and

—OC(O)NH(CH$_2$)$_2$SS(CH$_2$)$_2$NH—.

In another embodiment the linker region comprises a hydrolyzable ester. In a particular embodiment, the hydrolyzable ester is stable in the blood, but hydrolyzable by hydrolases (e.g., those present in the BBB).

In a particular embodiment, the linker moiety is completely cleaved or substantially cleaved, effecting the removal of the amphiphilic polymer from the polypeptide. In yet another embodiment, the linker moiety is completely cleaved or substantially cleaved resulting in the removal of the amphiphilic polymer from the polypeptide and most, if not all, of the linker region.

Additionally, the linkage between the polypeptide and the amphiphilic polymer can be a direct linkage between a functional group at a termini of the polymer and a functional group on the polypeptide.

Generally, the linker is a chemical moiety comprising a covalent bond or a chain of atoms that covalently attaches the therapeutic protein to the amphiphilic copolymer. The linker can be linked to any synthetically feasible position of the therapeutic polypeptide and the polymer. In a particular embodiment, the linker connects the at least one polymer of the instant invention and to a polypeptide via amine groups present on the polymer (e.g., on the termini or the R substituents) and polypeptide. In a particular embodiment the linker is attached at a position which avoids blocking the activity of the therapeutic protein. Exemplary linkers may comprise at least one optionally substituted; saturated or unsaturated; linear, branched or cyclic alkyl group or an optionally substituted aryl group. The linker may also be a polypeptide (e.g., from about 1 to about 20 amino acids, particularly about 1 to about 10). The linker may be biodegradable under physiological environments or conditions. The linker may also be non-degradable and may be a covalent bond or any other chemical structure which cannot be substantially cleaved or cleaved at all under physiological environments or conditions.

The instant invention also encompasses methods of synthesizing the polymer-agent conjugates of the instant invention. In a particular embodiment, the method comprises synthesizing or obtaining an amphiphilic copolymer of the instant invention with an amine group (e.g., an amine containing termini such as a piperazine group) and linking the amphiphilic copolymer with a polypeptide of interest via an amine reactive crosslinker (e.g., an amine-reactive N-hydroxysuccinimide (NHS)). The crosslinker may be reacted with the polypeptide first, with the polymer first, or with both simultaneously.

IV. Administration and Uses

The conjugation of the block copolymers of the instant invention to the agents of interest (e.g., polypeptide) enhances bioavailability and efficient transport across the histohematic barriers. The polymer-agent conjugates described herein also enhance delivery of the agent into cells. Accordingly, the instant invention encompasses methods of delivering an agent (e.g., a polypeptide) to a cell comprising operably linking the agent to a polymer of the instant invention and contacting the cell with the conjugate. The method can be performed in vitro or in vivo.

The polymer-agent conjugates described herein will generally be administered to a patient as a pharmaceutical preparation. The term "patient" as used herein refers to human or animal subjects. These polymer-agent conjugates may be employed therapeutically, under the guidance of a physician.

The compositions comprising the polymer-agent conjugates of the instant invention may be conveniently formulated for administration with any pharmaceutically acceptable carrier(s). For example, the conjugates may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the polymer-agent conjugates in the chosen medium may be varied and the medium may be chosen based on the desired route of administration of the pharmaceutical preparation. Except insofar as any conventional media or agent is incompatible with the polymer-agent conjugates to be administered, its use in the pharmaceutical preparation is contemplated.

The dose and dosage regimen of polymer-agent conjugates according to the invention that are suitable for administration to a particular patient may be determined by a physician considering the patient's age, sex, weight, general medical condition, and the specific condition for which the polymer-agent conjugate is being administered and the severity thereof. The physician may also take into account the route of administration, the pharmaceutical carrier, and the polymer-agent conjugate's biological activity.

Selection of a suitable pharmaceutical preparation will also depend upon the mode of administration chosen. For example, the polymer-agent conjugate of the invention may be administered by direct injection to a desired site. In this instance, a pharmaceutical preparation comprises the polymer-agent conjugate dispersed in a medium that is compatible with the site of injection.

Polymer-agent conjugates of the instant invention may be administered by any method. For example, the polymer-agent conjugates of the instant invention can be administered, without limitation parenterally, subcutaneously, orally, topically, pulmonarily, rectally, vaginally, intravenously, intraperitoneally, intrathecally, intracerbrally, epidurally, intramuscularly, intradermally, or intracarotidly. In a particular embodiment, the complexes are administered intravenously or intraperitoneally. Pharmaceutical preparations for injection are known in the art. If injection is selected as a method for administering the polymer-agent conjugate, steps must be taken to ensure that sufficient amounts of the molecules or cells reach their target cells to exert a biological effect. Dosage forms for oral administration include, without limitation, tablets (e.g., coated and uncoated, chewable), gelatin capsules (e.g., soft or hard), lozenges, troches, solutions, emulsions, suspensions, syrups, elixirs, powders/granules (e.g., reconstitutable or dispersible) gums, and effervescent tablets. Dosage forms for parenteral administration include, without limitation, solutions, emulsions, suspensions, dispersions and powders/granules for reconstitution. Dosage forms for topical administration include, without limitation, creams, gels, ointments, salves, patches and transdermal delivery systems.

Pharmaceutical compositions containing a polymer-agent conjugate of the present invention as the active ingredient in intimate admixture with a pharmaceutically acceptable carrier can be prepared according to conventional pharmaceutical compounding techniques. The carrier may take a wide variety of forms depending on the form of preparation desired for administration, e.g., intravenous, oral, direct injection, intracranial, and intravitreal.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of polymer-agent conjugates may be determined by evaluating the toxicity of the molecules or cells in animal models. Various concentrations of polymer-agent conjugates in pharmaceutical preparations may be administered to mice, and the minimal and maximal dosages may be determined based on the beneficial results and side effects observed as a result of the treatment. Appropriate dosage unit may also be determined by assessing the efficacy of the polymer-agent conjugate treatment in combination with other standard drugs. The dosage units of polymer-agent conjugate may be determined individually or in combination with each treatment according to the effect detected.

The pharmaceutical preparation comprising the polymer-agent conjugates may be administered at appropriate intervals, for example, at least twice a day or more until the pathological symptoms are reduced or alleviated, after which the dosage may be reduced to a maintenance level. The appropriate interval in a particular case would normally depend on the condition of the patient.

In a particular embodiment, the polymer-agent conjugate is administered to a cell of the body in an isotonic solution at physiological pH 7.4. However, the complexes can be prepared before administration at a pH below or above pH 7.4.

The instant invention encompasses methods of treating or diagnosing a disease/disorder comprising administering to a subject in need thereof a composition comprising a polymer-agent conjugate of the instant invention and, particularly, at least one pharmaceutically acceptable carrier. In a particular embodiment, the disease is cancer and the polymer comprises at least one chemotherapeutic agent. Other methods of treating the disease or disorder may be combined with the methods of the instant invention (e.g., other chemotherapeutic agents or therapy (e.g., radiation) may be co-administered with the compositions of the instant invention.

The following examples provide illustrative methods of practicing the instant invention, and are not intended to limit the scope of the invention in any way.

Example 1

Experimental Procedures
Materials and Methods

HRP type VI-A, MW 43 kDa, anhydrous methanol, dichloromethane, acetone, ethanol, N,N-dimethylformamide (DMF), N,N-diisoppropylethylamine (DIPEA), 2,4,6-trinitrobenzenesulfonic acid (TNBS), ultrapure urea, high resolution ampholyte (pH 3.5-10), trichloroacetic acid (TCA), o-phenylenediamine, proteinase K, and aprotinin were purchased from Sigma-Aldrich Co. (St-Louis, Mo.). Dithiobis (succinimidyl propionate) (DSP) and disuccinimidyl propionate (DSS) were purchased from Pierce Biotech Co. (Rockford, Ill.). Tris-HCl Precast gels (10%) were from Bio-Rad (Hercules, Calif.). Sephadex LH-20 gel was from GE Healthcare (Waukesha, Wis.). TSKgel® G3000SWXL column (7.8 mm ID×30 cm) was from Tosoh Co. (Japan). Amicon ultra-15 centrifugal filter, MWCO 30K, membrane NMWL was from Millipore Co. (Billerica, Mass.). Spectro/Por membrane (MWCO 2,000) was from Spectrum Lab Inc. (New Brunswick, N.J.). Flexible thin-layer chromatography (TLC) plates were from Whatman Ltd (Mobile, Ala.). All substances for polymer preparation were purchased from Aldrich (Steinheim, Germany) and Acros (Geel, Belgium) and were used as received unless otherwise stated. Methyl trifluoromethylsulfonate (MeOTf), 2-methyl-2-oxazoline (MeOx), 2-ethyl-2-oxazoline (EtOx), acetonitrile (CAN) and other solvents for polymer preparation were dried by refluxing over $CaH_2$ under dry nitrogen atmosphere and distilled prior to use. NMR spectra were recorded on a Bruker DRX 500 P, Bruker Avance III 400, Bruker ARX 300 or a Bruker AC 250 at room temperature. The spectra were calibrated using solvent signals ($CDCl_3$ 7.26 ppm, $D_2O$ 4.67 ppm). Gel permeation chromatography (GPC) was performed on a Waters system (pump mod. 510, RI-detector mod. 410, precolumn PLgel and two PL Resipore columns (3 µm, 300×7.5 mm)) with N,N-dimethylacetamide (DMAc) (57 mmol/L LiBr, 80° C., 1 mL/min) as eluent and calibrated against polymethylmethacrylate (PMMA) and polyethyleneglycol (PEG) standards. Alternatively a PL120 system using GRAM columns (Polymer Standards Services, Mainz, Germany) with dimethylacetamide (DMAc) (57 mmol/L LiBr, 70° C., 1 mL/min) was used.

Synthesis and Characterization of Poly(2-Oxazoline)s

The polymers were prepared according to previous accounts (Gaertner et al. (2007) J. Controlled Release, 119:291-300; Ivanova et al. (2008) Macromol. Chem. Phys., 209:2248-2258). Structures and analytical data of polymers are summarized in FIG. 1 and Table 1. Exemplarily for P(EtOX$_{50}$-b-BuOX$_{20}$), under dry and inert conditions 10 mg (61 µmol, 1 eq) of methyl trifluoromethylsulfonate (methyl triflate, MeOTf) and 321 mg (3.24 mmol, 53 eq) of 2-ethyl-2-oxazoline (EtOx) were dissolved in 3 mL dry acetonitrile at room temperature. The mixture was subjected to microwave irradiation (150 W maximum, 130° C.) for 5 minutes. After cooling to room temperature, the monomer for the second block, 2-butyl-2-oxazoline (157 mg, 1.23 mmol, 20 eq) were added and the mixture was irradiated the same way as for the first block. Finally the polymerization was terminated using 150 mg piperazine as a terminating reagent. For precipitation, a solvent mixture of cyclohexane and diethylether (50/50, v/v) was used. The product was obtained as a colorless solid (yield 0.36 g, 77%, $M_{th}$=7.8 kg/mol). GPC (DMAc): $M_n$=11.5 kg/mol (PDI 1.09); $^1$H-NMR (CDCl$_3$, 298 K): δ=3.45 (br, 276H, (NCH$_2$CH$_2$)); 3.04/2.95 (m, 3H, N—CH$_{3Ini}$); 2.5-2.2 (m, 144H, CO—CH$_2$—CH$_3$, CO—CH$_{2Pid}$); 1.58 (br, 37H, —CH$_2$—CH$_2$—CH$_2$—); 1.34 (br, 41H, —CH$_2$—CH$_3$); 1.11 (br, 151H, CO—CH$_2$—CH$_3$); 0.91 ppm (br, 56H, —CH$_{3butyl}$) $M_n$=7.5 kg/mol (EtOx$_{50}$-b-BuOX$_{19}$).

TABLE 1

Structure and analytical data of polymers used in this study.

| | Mn$^a$ | Mn (PDI)$^b$ | Yield$^d$ | CMC (w/w)$^e$ |
|---|---|---|---|---|
| PMeOx$_{50}$ | 4.3 | 5.5 (1.17) | 84 | n/a |
| P(EtOx$_{50}$-b-BuOx$_{20}$) | 7.8 | 11.5 (1.09) | 77 | 0.001 |
| | 6.9 | 11.0 (1.15) | 76 | 0.001 |
| P(EtOx$_{50}$-co-BuOx$_{20}$) | 7 | 9.3 (1.19) | 85 | 0.04 |
| P(MeOx$_{50}$-b-BuOx$_{20}$) | 7.1 | 5.5 (1.44)$^c$ | 80 | 0.002 |

$^a$Obtained from [M]$_0$/[I]$_0$.
$^b$As obtained by gel permeation chromatography.
$^c$Calibrated against polyethylene glycol standards on SDV columns (Polymer Standard services, Mainz, Germany).
$^d$Recovered yield after 2-3 precipitations.
$^e$Critical micelle concentration (CMC) in aqueous solution values at 37° C. as determined using pyrene probe.

Conjugation of HRP with Poly(2-Oxazoline)s

Amine terminated poly(2-oxazoline)s were reacted with small molecule linkers, disuccinimidyl propionate (DSS) or dithiobis (succinimidyl propionate) (DSP), under two different reaction conditions. Condition A: 110 mg of polymer in 0.5 mL of methanol were mixed with a 10-fold molar excess of DSS (DSP) in 0.5 mL of DMF stored over molecular sieves (4 Å). The mixture was supplemented with 0.1 mL sodium borate buffer (0.1M, pH 8) and incubated for 30 minutes at 25° C. Excess of DSS (DSP) was removed by gel filtration on a Sephadex LH-20 column (2.5×20 cm) in anhydrous methanol and solvent was removed in vacuo. Condition B: 110 mg of polymer and 10-fold molar excess of DSS (DSP) were dissolved in 1 mL of DMF stored over molecular sieves (4 Å). DIPEA (5 µL/10 mg polymer) was added as the organic base. The mixture was incubated for three days at 25° C. Work-up was performed as under condition A. $^1$H-NMR showed that within experimental error, 100% of polymers were conjugated with DSS or DSP. Activated polymer was subsequently dissolved in 1 mL 20% aqueous ethanol and mixed with 5 mg of HRP in 0.5 mL of 0.1M sodium borate (pH 8.0). The reaction mixture was incubated overnight at 4° C.

Purification of HRP-Poly(2-Oxazoline) Conjugates (HRPxPOx)

Purification of HRP conjugates has been described in previous studies (Yi et al. (2008) Bioconjug. Chem., 19:1071-1077; Batrakova et al. (2005) Bioconjug. Chem., 16:793-802). The HRP conjugates were precipitated in cold acetone to remove excess non-reacted polymers. Briefly, about 1 mL of the reaction mixture was added dropwise to 30 mL of cold acetone under stirring. HRP conjugates were precipitated and collected by centrifugation at 3000 rpm for 10 minutes at 4° C., washed by cold ethanol (10 mL) and dried in vacuo. The extent of elimination of non-reacted polymers was assayed by TLC on Silica Gel plates in dichloromethane/methanol (8:2). Under these conditions free polymers migrated ($R_f$=0.2), while the conjugate was immobile. To separate modified and unmodified HRP, the conjugates were further purified by TSKgel® G3000SWXL size exclusion column chromatography (0.78 cm×30 cm) using a mobile phase consisting of methanol (5%) and pH 6.8, 0.1 M NaH$_2$PO$_4$, 0.2 M NaCl buffer (95%). The final conjugates were desalted in an Amicon ultra-15 centrifuge tube (MWCO 30 kDa) and lyophilized.

SDS-PAGE Assay

Sodium dodecyl sulfate polyacrylamide gel electrophoresis (SDS-PAGE) was used to confirm the HRP conjugates which have a greater molecular weight than native protein. Briefly, 10 µg of native or modified HRP was mixed with 5× loading buffer (without DTT) and loaded into the 10% precast Tris-HCl gel. The analysis was performed in a Mini-PROTEAN® electrophoresis system (Bio-Rad, Hercules, Calif.) connected with PowerPac™ Basic Power Supply (Bio-Rad, Hercules, Calif.). The running condition was 85 V for 45 minutes and 100 V for 90 minutes. The gel was stained by Bio-Safe™ Coomassie stain (Bio-Rad, Hercules, Calif.) for 1 hour and destained in water.

Isoelectric Focusing (IEF) Assay

IEF was used to separate the HRP conjugates with different modification degrees based on their shifted isoelectric points. Briefly, denaturing IEF gel (pH 3.5-10) was prepared according to the literature (Bollag et al., Protein methods second edition. John Wiley & Sons, Inc. 174-183; Giulian et al. (1984) Anal. Biochem., 142:421-436). 20 µg of native or modified HRP was mixed with 2× loading buffer and loaded into the gel plate. The analysis was performed in a Mini-PROTEAN® electrophoresis system (Bio-Rad, Hercules, Calif.) connected with a PowerPac™ High-Voltage Power Supply (Bio-Rad, Hercules, Calif.). The running condition was 100 V for 1 hour, 200 V for 1 hour and 500 V for 30 minutes. The gel was fixed in 10% trichloroacetic acid (TCA) for 10 minutes and 1% TCA overnight. After fixing, the gel was stained by Bio-Safe™ Coomassie stain (Bio-Rad, Hercules, Calif.) for 1 hour and destained in water.

Degree of Modification by Trinitrobenzene Sulfonate (TNBS) Assay

A TNBS assay was used to determine the degree of protein modification according to the literature (Yi et al. (2008) Bioconjug. Chem., 19:1071-1077; Habeeb, A. F. S. A. (1965) Anal. Biochem., 14:328-336). Briefly, 10 µL of HRPxPOx solutions (protein concentration 0.1-0.6 mg/mL)

were mixed with 10 μL of TNBS solution (1.7 mM) in 80 μL of sodium borate buffer (0.1 M, pH 9.5) and incubated at 37° C. for 2 hours. The absorbance was measured at 405 nm using the microplate reader (Spectra Max, MDS, CA). The protein content was measured using a Micro BCA kit from Pierce (Rockford, Ill.). The degree of modification (average number of modified amino groups) was calculated according to the following equation:

$$S = 7 \times \frac{(A_{native}/C_{native} - A_{modified}/C_{modified})}{A_{native}/C_{native}} \quad (1)$$

where $A_{native}$ and $A_{modified}$ were the absorbencies and $C_{native}$ and $C_{modified}$ were the concentrations of native and modified HRP respectively. The total number of primary amino groups including lysine residues and terminal amine groups of HRP is seven (Yi et al. (2008) Bioconjug. Chem., 19:1071-1077).

Enzymatic Activity of HRPxPOx.

The use of o-phenylenediamine to determine the HRP enzymatic activity has been described in the literature (Yi et al. (2008) Bioconjug. Chem., 19:1071-1077; Slepnev et al. (1995) Bioconjug. Chem., 6:608-615). Briefly, 20 μL of 1 to 20 ng/mL HRPxPOx were added to 96-well plates and supplemented with 160 μL of citrate buffer (0.1 M, pH 5.0, containing 0.1% Triton X-100 and 1 mg/mL BSA). Freshly prepared o-phenylenedimine (0.5 mg/mL) in the same citrate buffer was mixed with 0.2% $H_2O_2$ and 20 μL of the mixture was added to each well immediately. After incubating at 37° C. for 5 minutes the reaction was stopped by 20 μL of a 0.5% $Na_2SO_3$ solution in 2N $H_2SO_4$, and the absorbance was measured at 490 nm using a microplate reader.

Circular Dichroism (CD) Spectra

Modified or unmodified HRP was dissolved in PBS (pH 7.4) at the concentration of 0.5 mg/mL determined by MicroBCA assay. Far-UV (200-260 nm) and near-UV-vis (250-450 nm) CD spectra were recorded using an Aviv Circular Dichroism Model 202SF spectrometer (Lakewood, N.J.) with a cuvette having a 1 cm path length. Spectra were obtained from 450 to 200 nm in 1 nm increments and the reported spectra correspond to the average of three wavelength scans. All the CD spectra of protein were obtained by subtracting the spectra of blank solvent. The mean residue molar ellipticity [θ] was calculated based on the following equation:

$$[\theta]=(\theta M)/(Cl) \quad (2)$$

where θ is the observed ellipticity (deg), M is the mean residue molecular weight (g/mol), C is the protein concentration (g/ml) and l is the optical path length (cm) (Goycoolea et al. (2009) Biomacromolecules 10:1736-1743).

Cellular Uptake.

HRP Binding.

MDCK cells (from ATCC, CCL-34) were seeded in 96-well plates at a density of 20,000 cells/well in Dulbecco's Modified Eagle Medium (DMEM) (Invitrogen, Carlsbad, Calif.) supplemented with 1% penicillin/streptomycin and 10% fetal bovine serum (Invitrogen, Carlsbad, Calif.). The cells were cultured at 37° C. with 95% humidity and 5% $CO_2$, and grown for two days until 80~90% confluence. Caco-2 cells (from ATCC, HTB-37) were seeded in collagen-coated 96-well plates at a density of 5000 cells/well and grown to 80% confluence (5-6 days) in the same medium and culture conditions as MDCK. The cells were washed twice in assay buffer containing 122 mM NaCl, 25 mM $NaHCO_3$, 10 mM glucose, 3 mM KCl, 1.2 mM $MgSO_4$, 0.4 mM $K_2HPO_4$, 1.4 mM $CaCl_2$ and 10 mM HEPES. Cells were exposed to unmodified or modified HRP in assay buffer for various time intervals (10 to 120 minutes) at 37° C., then washed with cold phosphate-buffered saline 5 times and lysed in 1% Triton X-100. No cellular toxicity was observed during the treatment. Aliquots of cell lysates (20 μL) were taken for HRP activity determination as described above. Separate calibration curves were used for unmodified and modified HRP. The amounts of cell associated HRP were normalized for the cell protein as determined by MicroBCA assay.

HRP Internalization.

The method to determine the internalized HRP has been described in the literature (7). Briefly, Caco-2 cells were exposed to unmodified or modified HRP in assay buffer for 30 minutes at 37° C., then washed with cold phosphate-buffered saline 5 times, and incubated 60 minutes with proteinase K (0.1 mg/ml) in assay buffer at 4° C. The medium was replaced by assay buffer containing aprotinin (10 U/mL) for 10 minutes, then the cells were washed by cold phosphate-buffered saline 3 times and lysed in 1% Triton X-100. HRP activity and concentration were determined as stated hereinabove.

Statistical Analysis

Statistical analysis was performed using one-way ANOVA (LSD multiple comparisons). A minimum p value of 0.05 was estimated as the significance level for all tests.

Results and Discussion

Synthesis and Purification of HRPxPOx

The synthetic routes for HRPxPOx are presented in FIG. 6. Four different POx were used for the conjugation: three copolymers of MeOx or EtOx as hydrophilic monomers and BuOx as hydrophobic monomer P(MeOx-b-BuOx), P(EtOx-b-BuOx) and P(EtOx-co-BuOx)) and one homopolymer (PMeOx). These polymers were designed that the amount of BuOx was comparable for all three copolymers and that the degree of polymerization of the respective hydrophilic monomer was comparable in all of the four polymers. The secondary amine in the terminal piperazine group of the polymers was coupled to the primary amine of HRP using small bi-functional linkers, disuccinimidyl propionate (DSS) or dithiobis (succinimidyl propionate) (DSP). DSS is a non-degradable linker, while DSP contains a disulfide bond, and is stable in the extracellular media but usually cleaves in the reducing environment of the cell (Colcher et al. (1998) Q. J. Nucl. Med., 42:225-241). First, the polymers were reacted with the linkers to generate N-hydroxysuccinimide-terminated polymer reagents. Second, the activated polymers were then reacted with HRP in 20% aqueous ethanol. For this reaction, pH 8.0 was selected based on previous experience with HRP-Pluronic conjugation (Yi at al. (2008) Bioconjug. Chem., 19:1071-1077). The HRPxPOx polymers were purified first by cold acetone precipitation and then by size exclusion chromatography (FIG. 2).

Characterization of HRPxPOx.

Analytical data of the HRPxPOx polymers are summarized in Table 2. The typical mean modification on degree of HRP conjugates obtained ranged from ca. 0.7 [for P(MeOx-b-BuOx) and P(EtOx-co-BuOx)] to ca. 1.6 [for P(MeOx-b-BuOx)] polymer chains per protein as determined by TNBS titration of the protein free amino groups. In most cases the residual enzymatic activity of HRP after conjugation was relatively high (70%-90%). The conjugation of polymer was further confirmed by SDS-PAGE. The high resolution IEF was used to separate protein conjugates with different isoelectric points (Snider et al. (1992) J. Chromatography 599:141-155). IEF produced better separation of HRPxPOx with different modification degrees than SDS-PAGE (FIGS. 3A and 3B). As shown in FIG. 3, after conjugation, the predominant band of HRP is not visible and distinct bands of protein modified with different number of polymer chains can be seen in IEF (FIG. 3B, lanes E, F). This reinforces the proposition that modification degrees determined by TNBS assay provide the mean values and the conjugate samples contain mixtures of HRP with different modification degrees (Yi at al. (2008) Bioconjug. Chem., 19:1071-1077). Simple mixing of protein and polymer did not change the electrophoretic mobility of HRP (FIG. 3B, lanes C, D).

TABLE 2

Characteristics of HRP-poly(2-oxazoline) conjugates.

| Conjugate | Linker | Experimental Condition[a] | Modification Degree | Residual Activity |
|---|---|---|---|---|
| HRPxP (MeOx-b-BuOx)* | DSS | B | 1.62 | 87.0% |
| HRPx$^{SS}$P (MeOx-b-BuOx) | DSP | A | 0.67 | N/D |
| HRPxP (EtOx-b-BuOx)* | DSS | B | 1.04 | 76.8% |
| HRPx$^{SS}$P (EtOx-b-BuOx) | DSP | A | 1.16 | 70.1% |
| HRPxP (EtOx-co-BuOx)* | DSS | B | 0.76 | 77.9% |
| HRPxPMOx* | DSS | B | N/D | 87.5% |

[a]Condition A: Reaction was conducted in 500 µL methanol, 500 µL DMF, and 100 µL sodium borate buffer (pH 8.0), at room temperature for 30 minutes; Condition B: 1 mL DMF and 5 µL (per 10 mg polymer) DIPEA, at room temperature for 3 days.
*Those conjugates were used for CD analysis and cellular uptake studies.

Conformation Stability.

Possible changes of secondary and tertiary structure of a protein during chemical modification may lead to aggregation and deactivation (McNally, E. J., Protein formulation and delivery first edition. Marcel Dekker, Inc. 31-41). Therefore, the HRP structure was examined after modification by CD spectroscopy. Both Far-UV (190-260 nm) and Near-UV (250-300 nm) CD spectra of HRP and HRPxPOx were recorded and analyzed (FIG. 4). The Far-UV CD spectra of the conjugates revealed considerable CD signal decreases in the major bands at 215 nm and 225 nm and a shift of 225 nm band to 230 nm compared to unmodified protein (FIG. 4A). These CD changes were most pronounced for HRPxP (MeOx-b-BuOx) and are indicative of changes in the secondary structure of the HRP apo-protein (Akita et al. (2001) Biosci. Biotechnol. Biochem., 65:1581-1588; Strickland, E. H., (1968) Biochem. Biophys. Acta., 151:70-75). At the same time there was little change to the CD signal in the Near-UV spectra of the conjugates (FIG. 48). This suggests that the tertiary structure of HRP apo-protein and the microenvironment of the prosthetic heme remain unaffected by the conjugation (Akita et al. (2001) Biosci. Biotechnol. Biochem., 65:1581-1588; Strickland, E. H., (1968) Biochem. Biophys. Acta., 151:70-75), even though the secondary structure may be ascribed to possible interactions between the block copolymer chain and α-helices on the surface of the apo-protein. This interaction may be responsible for the partial loss of the enzyme activity after the modification. However, the enzyme was still catalytically active as its tertiary structure was more robust due to the presence of stabilizing structural elements (two $Ca^{2+}$ ions and four disulfide bridges) in HRP molecules (Tsaprailis et al. (1998) Biochemistry 37:2004-2016).

Cellular Uptake of HRPxPOx.

The cellular uptake of the HRPxPOx was examined using MDCK and Caco-2 cell models. The cells were exposed to the unmodified protein or the conjugates (50 µg/mL) for different time intervals (up to 120 minutes) and the total amounts of HRP bound with cell membranes or internalized into cells were measured as described (Slepnev et al. (1995) Bioconjug. Chem., 6:608-615). In both cell models HRPxP (MeOx-b-BuOx) exhibited significant enhanced cellular uptake (3-6 fold) compared to unmodified protein ($p<0.01$) and other conjugates ($p<0.05$). The increase in uptake was also observed for HRPxP(EtOx-BuOx) conjugate (2-3 fold, $p<0.05$) but it was not statistically significant at 60 minutes for MDCK cells or 60 min and 80 min for Caco-2 cells. The conjugate of HRP with a random copolymer, HRPxP(EtOx-co-BuOx), did not show any uptake increase in MDCK cells but demonstrated an uptake increase in Caco-2 cells ($p<0.05$ at 60 minutes). A conjugate with a hydrophilic copolymer, HRPxPMOx, exhibited a similar cellular uptake to unmodified HRP in Caco-2 cells, and even lower uptake in MDCK cells ($p<0.1$, marginally significant). A simple mixing of HRP and polymers at 1:10 (molar ratio) did not show any effect on the uptake.

Furthermore, HRPxP(EtOx-b-BuOx) and HRPxPMeOx were chosen to identify the amount of protein which was adsorbed on the cell surface and which internalized into the cells, respectively. Caco-2 cells were treated with proteinase K to remove the protein bound with cell membrane after being incubated with HRP and HRPxP(EtOx-b-BuOx) and HRPxPMeOx for 30 minutes. The amounts of internalized protein were then quantified and compared (Table 3). HRPxP(EtOx-b-BuOx) exhibited both increased adsorption and internalization compared to unmodified protein, while HRPxPMeOx demonstrated greater cell binding, but much lower cell internalization. The structure of copolymers has a marked influence on the cellular uptake presumably by altering the interaction with the cellular membrane (Barz et al. (2009) Biomaterials 30:5682-5690.).

TABLE 3

Distribution of HRP and HRPxPOx in Caco-2 Cells.

| | Cell-Bound HRP[a] (ng/mg Total Protein) | | |
|---|---|---|---|
| Samples | Total Uptake | Adsorption | Internalization |
| HRP | 87.8 | 10.0 | 67.8 |
| HRPxP (EtOx-b-BuOx) | 165.0 | 62.4 | 102.6 |
| HRPxPMeOx | 75.6 | 52.4 | 23.2 |

[a]50 µg/mL HRP or HRP conjugates was incubated with Caco-2 cells for 30 minutes at 37° C. Internalized protein was determined after proteinase K treatment. HRP adsorbed was calculated as the difference between total uptake and internalized protein.

Similarly, previous studies of HRP conjugates with Pluronic® block copolymers suggest that the relative lengths of hydrophilic block and hydrophobic blocks of the copolymer have a major effect on the cellular uptake of such HRP conjugates (Yi et al. (2008) Bioconjug. Chem., 19:1071-1077.). Long hydrophobic blocks can increase the non-specific binding of protein with the cell membrane but also cause possible aggregation. A shorter hydrophilic block is more desirable in terms of cellular uptake but its length should be carefully chosen in order to avoid possible protein conjugate instability. However, in the case of copolymer conjugates, the highest uptake for HRPxP(MeOx-b-BuOx)

was observed with more hydrophilic polymer in the hydrophilic block followed by the slightly less hydrophilic HRPxP (EtOx-b-BuOx) and the respective random version HRPxP (EtOx-co-BuOx). It is interesting that HRPxP(MeOx-b-BuOx) displays greater cellular uptake than HRPxP(EtOx-b-BuOx). Both block copolymers have a comparable hydrophobic block while the PMeOx block is more hydrophilic than PEtOx. The higher modification degree of HRPxP(MeOx-b-BuOx) (1.62) compared to HRPxP(EtOx-b-BuOx) (1.04) may be responsible for the difference in uptake. The uptake of the latter two conjugates, HRPxP (EtOx-b-BuOx) and HRPxP(EtOx-co-BuOx), is still comparable in the case of Caco-2 cells. The relatively low levels of uptake of HRPxP(EtOx-co-BuOx) compared to HRPxP (EtOx-b-BuOx) in MDCK cells may suggest that a random copolymer without ordered block structure, while being surface active, cannot elicit appropriate interactions of the conjugates with the cellular membrane to increase cellular uptake in some cell lines. The cellular uptake of polymer aggregates with respect to the polymer microstructure was recently reported (Barz et al. (2009) Biomaterials 30:5682-5690). In that case, markedly higher uptake for the random copolymers was found. However, these systems were of a different polymer (poly(2-hydroxypropyl)acrylamide) and without proteins. Hydrophilic flexible polymers such as PEG, PMeOx and PEtOx are well known to enhance water solubility of covalently attached molecules such as drugs and protein while reducing their interaction with other proteins, surfaces and interfaces. Therefore, reduced cellular uptake of HRPxPMeOx is expected.

Thus, HRP-poly(2-oxazoline) conjugates were successfully synthesized with different polymer structures and linkers, using a well established conjugation procedure. These conjugates bear 0.7 or 1.7 polymer moieties per protein and retain high enzymatic activity of the native HRP. Conformation analysis reveals that polymer modification changed the secondary structure, but not the tertiary structure and heme environment of HRP important for the catalytic activity. HRPxP(MeOx-b-BuOx) and HRPxP(EtOx-b-BuOx) showed significantly enhanced cellular uptake in MDCK cells and Caco-2 cells, which was not found in HRPxP (EtOx-co-BuOx) and HRPxPMOX conjugates. The inability of these two polymer conjugates to increase cellular uptake is possibly due to the lack of structural ordered hydrophobic block which can assist the hydrophilic protein to bind with the cell membrane. Combined, these data indicate that modification by amphiphilic block copolymer is a useful strategy to enhance cellular delivery and transport of protein drugs.

Example 2

SOD-POx Conjugation

P(MeOx-b-BuOx) and P(EtOx-b-BuOx) were further investigated. A macromolecular antioxidant, superoxide dismutase 1 (SOD1, Cu/Zn SOD), was chosen for POx conjugation because of its therapeutic potential in multiple human diseases such as stroke and hypertension. POx were conjugated with SOD by biodegradable (DSP) or non-biodegradable (DSS) linkers. The SOD-POx conjugates were characterized by electrophoresis, isoelectric focusing (IEF), TNBS assay, MALDI-TOF, CD and enzymatic activity assays. The cellular binding and uptake of these conjugates were quantitatively determined and compared in MDCK cells and CATH.a neuronal cells, using an established SOD ELISA method.

SOD-POx conjugates were prepared using a two-step synthesis route and purified by HPLC (FIG. 6B). MALDI-TOF, PAGE and IEF analysis confirmed the success of polymer conjugation (FIG. 7 and FIG. 8). The conjugates contained approximately five to eight polymer chains per enzyme and 5% to 20% of the enzymatic activity was retained in most cases. These results are summarized in Table 4. Far-UV CD spectra reveal that the secondary structures of protein were well preserved after modification (FIG. 9). ELISA analysis shows that cellular uptake of SOD-P(MeOx-b-BuOx) and SOD-P(EtOx-b-BuOx) significantly increased compared to unmodified SOD ($p<0.01$ for MDCK and $p<0.001$ for CATH.a) and PEGylated SOD ($p<0.05$ for MDCK and $p<0.001$ for CATH.a) (FIG. 10).

TABLE 4

Characteristics of SOD-POx conjugates

| Conjugates | Linker | Modification degree (by TNBS assay) | Remaining activity (%) (by pyrogallol auto-oxidation assay) |
|---|---|---|---|
| SOD-P (MeOx-b-BuOx) | DSS | 6.76 | 19.41 |
| SOD-P (MeOx-b-BuOx) | DSP | 6.22 | 12.33 |
| SOD-P (EtOx-b-BuOx) | DSS | 6.03 | 6.04 |
| SOD-P (EtOx-b-BuOx) | DSP | 5.71 | 8.24 |

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A polymer-polypeptide conjugate comprising at least one amphiphilic block copolymer linked to at least one polypeptide,
wherein said amphiphilic block copolymer comprises at least one hydrophilic segment and at least one hydrophobic segment, wherein said hydrophilic segment is a hydrophilic poly(2-oxazoline), wherein said hydrophobic segment is a hydrophobic poly(2-oxazoline), and wherein said amphiphilic block copolymer comprises the formula:

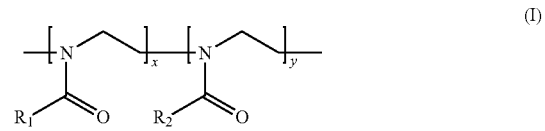

(I)

wherein x and y are independently selected between 10 and about 100; one of $R_1$ and $R_2$ is selected from the group consisting of —H, —OH, —NH$_2$, —SH, —CH$_3$, —CH$_2$CH$_3$, and an alkyl comprising 1 or 2 carbon atoms; and the other R group is an alkyl or an aryl.

2. The conjugate of claim 1, wherein said hydrophilic segment is poly(2-methyl-2-oxazoline) or poly(2-ethyl-2-oxazoline).

3. The conjugate of claim 1, wherein said hydrophobic segment is poly(2-butyl-2-oxazoline).

4. The conjugate of claim 1, wherein said polypeptide is a therapeutic agent, a diagnostic agent, or a cosmetic agent.

5. The conjugate of claim 1, wherein said amphiphilic block copolymer is linked to said polypeptide via a linker.

6. The conjugate of claim 1, wherein said amphiphilic block copolymer is covalently linked to said polypeptide.

7. The conjugate of claim 1, wherein said amphiphilic copolymer comprises the formula:

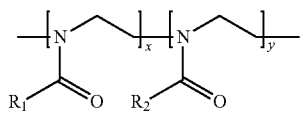 (I)

wherein $R_1$ is selected from the group consisting of —H, —OH, —NH$_2$, —SH, —CH$_3$, —CH$_2$CH$_3$, and an alkyl comprising 1 or 2 carbon atoms; and $R_2$ is an alkyl or an aryl.

8. A composition comprising at least one conjugate of claim 1 and at least one carrier.

9. The conjugate of claim 1, wherein said polypeptide is linked to a terminus of said amphiphilic block copolymer.

10. The conjugate of claim 5, wherein said polypeptide is linked to a terminus of said amphiphilic block copolymer via said linker.

11. The conjugate of claim 1, wherein said hydrophilic segment is poly(2-methyl-2-oxazoline) or poly(2-ethyl-2-oxazoline) and wherein said hydrophobic segment is poly(2-butyl-2-oxazoline).

12. The conjugate of claim 11, wherein said amphiphilic block copolymer is (2-methyl-2-oxazoline)$_{50}$-(2-butyl-2-oxazoline)$_{20}$ or (2-ethyl-2-oxazoline)$_{50}$-(2-butyl-2-oxazoline)$_{20}$.

13. The conjugate of claim 11, wherein said polypeptide is linked to a terminus of said amphiphilic block copolymer via said linker and wherein said polypeptide is superoxide dismutase.

14. The conjugate of claim 12, wherein said polypeptide is linked to a terminus of said amphiphilic block copolymer via said linker and wherein said polypeptide is superoxide dismutase.

15. The conjugate of claim 13, wherein said linker is non-biodegradable.

16. The conjugate of claim 14, wherein said linker is non-biodegradable.

17. The conjugate of claim 5, wherein said linker is non-biodegradable.

18. The conjugate of claim 1, wherein said polypeptide is linked to a terminus of said hydrophobic segment of said amphiphilic block copolymer.

19. The conjugate of claim 5, wherein said polypeptide is linked to a terminus of said hydrophobic segment of said amphiphilic block copolymer via said linker.

20. The conjugate of claim 11, wherein said polypeptide is linked to the terminus of said poly(2-butyl-2-oxazoline).

* * * * *